United States Patent
Pewzner et al.

(10) Patent No.: US 7,130,672 B2
(45) Date of Patent: Oct. 31, 2006

(54) APPARATUS AND METHOD FOR MONITORING TISSUE VITALITY PARAMETERS

(75) Inventors: Eliahu Pewzner, Modiin Ilit (IL); Avraham Mayevsky, Ramat Gan (IL)

(73) Assignee: Critisense Ltd., Givat-Shmuel (IL)

(*) Notice: Subject to any disclaimer, the term of this patent is extended or adjusted under 35 U.S.C. 154(b) by 116 days.

(21) Appl. No.: 10/381,383

(22) PCT Filed: Sep. 25, 2001

(86) PCT No.: PCT/IL01/00906

§ 371 (c)(1),
(2), (4) Date: Mar. 25, 2003

(87) PCT Pub. No.: WO02/24048

PCT Pub. Date: Mar. 28, 2002

(65) Prior Publication Data

US 2004/0054270 A1    Mar. 18, 2004

(51) Int. Cl.
*A61B 5/00* (2006.01)
*A61B 5/02* (2006.01)

(52) U.S. Cl. .................. 600/324; 600/326; 600/310; 600/504

(58) Field of Classification Search ........ 600/309–310, 600/322–323, 473, 476, 324, 326, 504
See application file for complete search history.

(56) References Cited

U.S. PATENT DOCUMENTS

| | | | |
|---|---|---|---|
| 4,109,647 A | 8/1978 | Stern et al. | |
| 4,449,535 A | 5/1984 | Renault | |
| 4,703,758 A | 11/1987 | Omura | |
| 4,945,896 A | 8/1990 | Gade | |
| 5,042,494 A | 8/1991 | Alfano | |
| 5,201,318 A | 4/1993 | Rava et al. | |
| 5,318,022 A | 6/1994 | Taboada et al. | |
| 5,551,422 A * | 9/1996 | Simonsen et al. | 600/322 |
| 5,685,313 A | 11/1997 | Mayevsky | |
| 5,770,454 A * | 6/1998 | Essenpreis et al. | 436/164 |
| 5,916,171 A | 6/1999 | Mayevsky | |

FOREIGN PATENT DOCUMENTS

| | | |
|---|---|---|
| EP | 0 442 011 | 9/1991 |
| GB | 2311854 | 10/1997 |
| WO | WO98/44839 | 10/1998 |
| WO | WO99/02956 | 1/1999 |
| WO | WO99/59464 | 11/1999 |

OTHER PUBLICATIONS

Stern, M.D.; "In Vivo Evaluation of Microcirculation by Coherent Light Scattering"; Mar. 6, 1975; Nature; vol. 254; pp. 56-58.

(Continued)

*Primary Examiner*—Eric F. Winakur
(74) *Attorney, Agent, or Firm*—Fenster & Company

(57) ABSTRACT

Apparatus for monitoring a plurality of tissue viability parameters of a tissue layer element, in which two different illumination sources are used via a common illumination element in contact with the tissue. One illumination source is used for monitoring blood flow rate and optionally flavoprotein concentration, and collection fibers are provided to receive the appropriate radiation from the tissue. The other illuminating radiation is used for monitoring any one of and preferably all of NADH, blood volume and blood oxygenation state of the tissue element, and collection fibers are provided to receive the appropriate radiation from the tissue. In one embodiment, the wavelengths of the two illumination sources are similar, and common collection fibers for the two illuminating radiations are used. In another embodiment, the respective collection fibers are distanced from the illumination point at different distances correlated to the ratio of the first and second illuminating wavelengths.

52 Claims, 16 Drawing Sheets

OTHER PUBLICATIONS

Chance, B. et al; "Respiratory Enzymes in Oxidative Phosphorylation"; 1955; J. Biol. Chem.; pp. 383-393.

Kramer R.S. et al; "Cerebral Cortical Microfluorometry at Isobestic Wavelengths for Correction of Vascular Artifact"; Aug. 17, 1979; Science; vol. 205; pp. 693-696.

Pologe, J.; "Pulse Oximetry: Technical Aspects of Machine Design"; 1987; Int. Anesthesiol. Clin.; vol. 25(3); pp. 137-153.

Rampil, I., et al; "Correlated, Simultaneous, Multiple-Wavelength Optical Monitoring In Vivo of Localized Cerebrocortical NADH and Brain Microvessel Hemoglobin Oxygen Saturation"; Jul. 1992; Journal of Clinical Monitoring; vol. 8; pp. 216-225.

Kessler, M. et al; "Quantitative Spectroscopy in Tissue"; Nov. 15-16, 1988; Proceeding of the Workshop on Quantitative Spectroscopy in Tissue; 10 pages.

Kobayashi, S. et al; "Optical Consequences of Blood Substitution on Tissue Oxidation-Reduction State Microfluorometry"; Jun. 1971; J. Appl. Physiol.; vol. 31; No. 1; pp. 93-96.

Renault, G. et al; "In situ Double Beam NADH Laser Fluorimety: choice of a reference wavelength"; Copyright 1984; American Physiological Society; pp. H491-H499.

Mayevsky, A. et al; "Repetitive Patterns of Metabolic Changes During Cortical Spreading Depression of the Awake Rat"; Brain Research; vol. 65; pp. 529-533.

Harbig, K., et al; "In vivo Measurement of Pyridine Nucleotide Fluorescence from Cat Brain Cortex"; Oct. 1976; J. Appl. Physiol.; vol. 41; No. 4; pp. 480-488.

Jobsis, F., et al; "Intracellular Redox Changes in Functioning Cerebral Cortex I. Metabolic Effects of Epileptiform Activity"; 1971; Neurophysiology; vol. 3465; pp. 735-749.

Taitelbaum, H.; "Optical Penetration Depth in Layered Tissues"; 1994; OSA Proceeding on Advances in Optical Imaging and Photon Migration; vol. 21; pp. 305-309.

Eggert, H., et al; "Optical Properties of Human Brain Tissue, Meninges,and Brain Tumors in the Spectral Range of 200 to 900 nm"; Copyright 1987; Neurosurgery; vol. 21; No. 4; pp. 459-464.

American National Standard; "American National Standard for Safe Use of Lasers"; 2000; ANSI Z136.1; pp. i., ii., 41-50.

International Standard; "Safety of Laser Products"; 2001; IEC 60825-1; Edition 1.2; 5 pages.

Kobayashi, S., et al; "Microfluorometry of Oxidation-Reduction Rate of the Rat Kidney in situ"; Nov. 1971; J. Appl. Physiol.; vol. 31; No. 5; pp. 693-696.

Anderson, R. et al; "Microvasculature Can be Selectively Damaged Using Dye Lasers: A Basic Theory and Experimental Evidence in Human Skin"; 1981; Lasers in Surgery and Medicine; vol. 1; pp. 263-276.

* cited by examiner

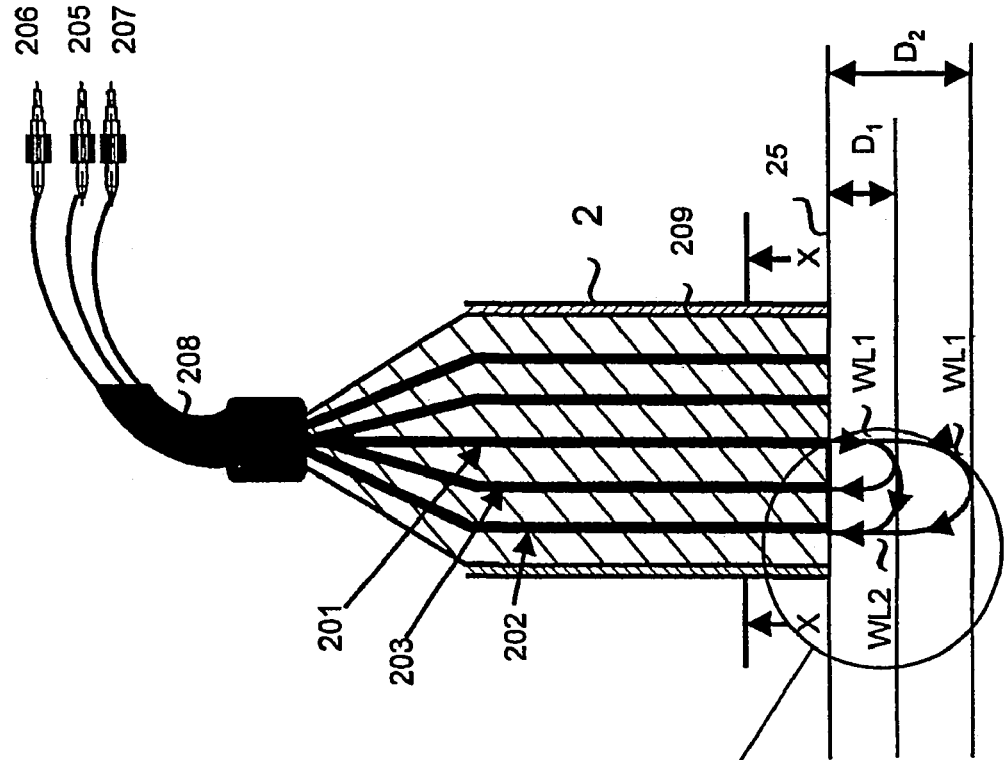

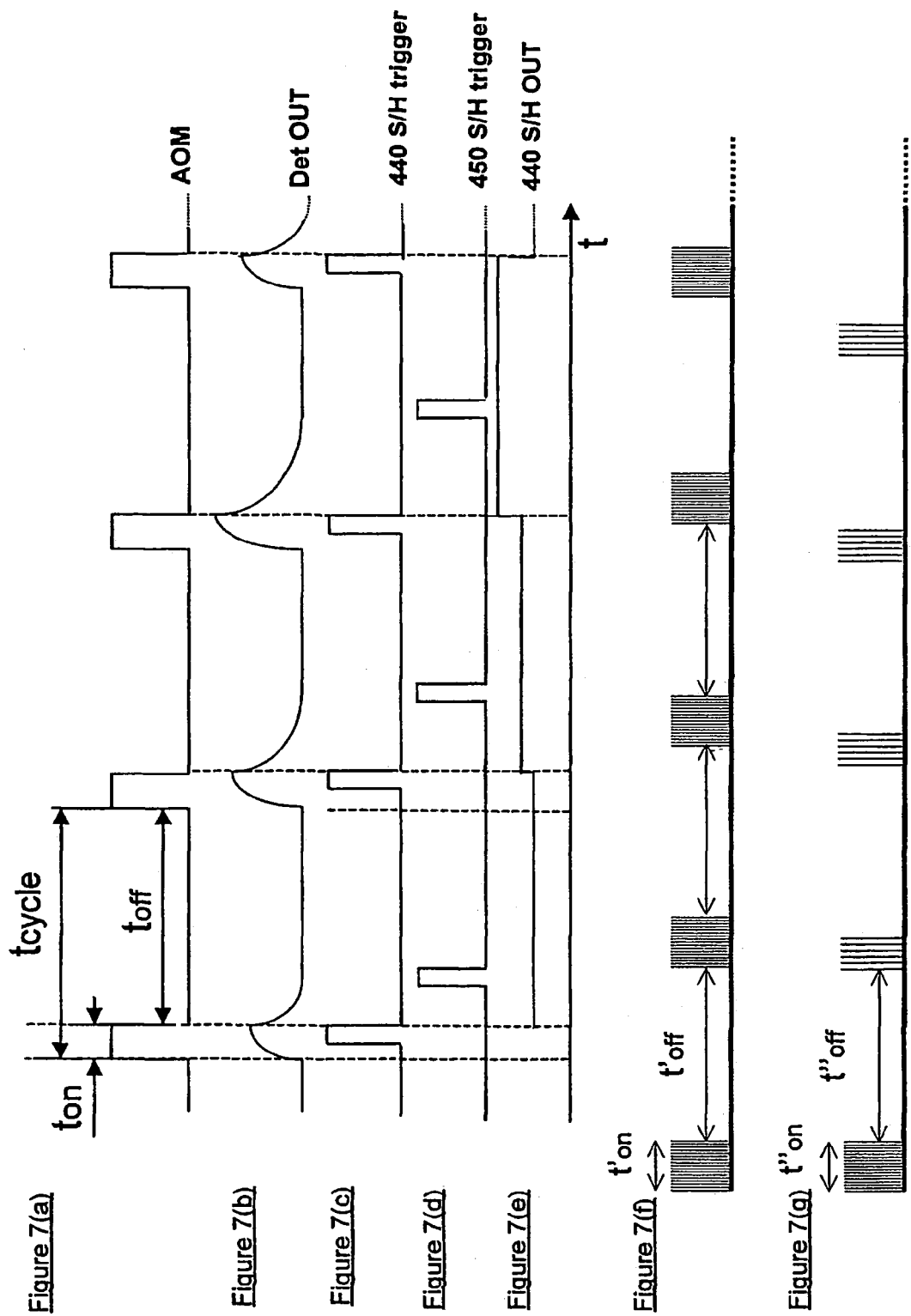

APPARATUS AND METHOD FOR MONITORING TISSUE VITALITY PARAMETERS

RELATED APPLICATIONS

This application is a U.S. national phase of PCT application PCT/IL01/00906, filed Sep. 25, 2001, which claims priority from Israel application IL 138683, filed Sep. 25,2000.

FIELD OF THE INVENTION

The present invention relates to apparatuses and methods for enabling simultaneous, pseudo-simultaneous, or individual monitoring of a plurality of tissue vitality parameters, particularly in-vivo, with respect to an identical tissue layer element or volume. In particular, such parameters include blood flow rate, NADH concentration, blood volume, blood oxygenation state and flavoprotein concentration.

BACKGROUND

Mammalian tissues are dependent upon the continuous supply of oxygen and glucose needed for the energy production. This energy is used for various types of work, including the maintaining of ionic balance and biosynthesis of various cellular components. The ratio or balance, between oxygen supply and demand reflects the cells' functional capacity to perform their work. In this way, the energy balance reflects the metabolic state of the tissue. In order to assess the tissue energy balance, it is necessary to monitor the events continuously using a multiparametric system in real-time.

The integrated system of energy supply and demand can be understood by considering the various components thereof.

$O_2$ supply: The blood carries the oxygen and other essential substances to the cells. Therefore, monitoring of blood flow rate, blood volume and blood oxygenation will reflect the supply of $O_2$ to the tissue for the purpose of energy formation therein.

Energy production and demand: In an inner compartment of the cells, called the mitochondria, the glucose and $O_2$ are transformed into ATP, a form of energy which can be used by the cells for various types of activities. The ATP production rate is, in normal states, regulated by rate of consumption of ATP, and is increased when cellular activity rises. In most pathological states, the limiting factor for this process is $O_2$ availability.

The process of energy (ATP) production and consumption can be determined through monitoring of Nicotineamide adenine dinucleotide (NADH) redox state. The NADH and NAD molecules can be correlated with the process of ATP production. The concentration of the reduced form of the molecule (NADH) rises when the rate of ATP production is low, and is unable to meet the demand in the tissue or cells.

A complementary indicator of energy production, other than NADH, is the concentration of flavoproteins (Fp). Flavoprotein molecules are also linked to the production of ATP in the mitochondria. Fp concentration drops when the rate of ATP production is reduced, and is unable to meet the demand in the tissue or cells.

There is direct correlation between energy metabolism of the cellular compartment and the blood flow in the microcirculation of the same tissue. In a normal tissue, any change in the $O_2$ demand will be compensated by a corresponding change in the blood flow to the tissue. By this mechanism, the $O_2$ supply remains constant if there is no change in the $O_2$ consumption. Any change in the abundance of $O_2$ in the tissue, in other words a change in energy state, will be reflected by the NADH and Fp level.

It is important to monitor both supply and demand in order to be able to detect pathological situations in which the balance is disrupted, and one component of the system reacts abnormally with respect to the other.

The parameters used in the art for the assessment of tissue vitality include: A—Blood Flow Rate; B—Mitochondrial Redox State via the NADH level; C—Blood Volume; D—Blood Oxygenation State; E—Mitochondrial Redox State via flavoprotein level.

A—Blood Flow Rate

The blood flow rate relates to the mean volume flow rate of the blood and is essentially equivalent to the mean velocity multiplied by the number of moving red blood cells in the tissue. This parameter may be monitored by a technique known as Laser Doppler Flowmetry, which is based on the fact that light reflected off moving red blood cells (RBC) undergoes a small shift in wavelength (Doppler shift) in proportion to the cell's velocity. Light reflected off of stationary RBC or bulk stationary tissue, on the other hand, does not undergo a Doppler shift.

By illuminating with coherent light, such as a laser, and converting the intensities of incident and reflected light to electrical signals, it is possible to estimate the blood flow from the magnitude and frequency distribution of those signals (U.S. Pat. No. 4,109,647; Stern, M. D. Nature 254, 56–58, 1975).

B—Mitochondrial Redox State or the NADH Level

The level of Nicotineamide adenine dinucleotide (NADH), the reduced form of NAD, is dependent both on the availability of oxygen and on the extent of tissue activity. Referring to FIG. 1, whilst NADH absorbs UV light at wavelengths of about 300 nm to about 400 nm and fluoresces at wavelengths of about 400 nm to about 550 nm, the NAD does not fluoresce. The NADH Level can thus be measured using Mitochondrial NADH Fluorometry. The conceptual foundations for Mitochondrial NADH Fluorometry were established in the early 50's and were published by Chance and Williams (Chance B., & Williams G. R., Journal of Biological Chemistry, 217, 383–392, 1955). They defined various metabolic states of activity and rest for in-vitro mitochondria.

An increase in the level of NADH with respect to NAD and the resulting increase in fluorescence intensity indicate that insufficient Oxygen is being supplied to the tissue. Similarly, a decrease in the level of NADH with respect to NAD and the resulting decrease in fluorescence intensity indicate an increase in tissue activity.

C—Blood Volume

The blood volume parameter refers to the concentration of the blood in the tissue. When tissue is irradiated, the intensity R of reflection of the excitation wavelength light from the tissue is informative of the blood volume. The intensity R of the reflected signal, also referred to as the total backscatter, increases dramatically as blood is eliminated from the tissue as a result of the decrease in haemoglobin concentration. Similarly, if the tissue becomes more perfused with blood, R decreases due to the increase in the haemoglobin concentration.

D—Blood Oxygenation State

The blood oxygenation state parameter refers to the relative concentration of oxyhaemoglobin to deoxy-haemoglobin in the tissue. It may be assessed by the performance of photometry measurements. The absorption spectrum of oxyhaemoglobin $HbO_2$ is considerably different from the absorption spectrum of deoxy-haemoglobin Hb (Kramer R. S. and Pearlstein R. D., Science, 205, 693–696, 1979). The measurement of the absorption at one or more wavelengths can thus be used to assess this important parameter. Blood oximeters are based on measurement of the haemoglobin absorption changes as blood deoxygenates (Pologe J. A., Int. Anesthesiol. Clin., 25(3), 137–53, 1987). Such oximeters generally use at least two light wavelengths to probe the absorption. One known method uses one wavelength at an isosbestic point and another wavelength at a point that exhibits absorption changes due to variation in oxygenation level. Another technique uses wavelengths at both sides of an isosbestic point in order to increase measurement sensitivity. The wavelengths used in commercial pulse oximeters are typically around 660 nm in the red region of the spectrum, and between 800 to 1000 nm in near-infrared region (Pologe, 1987).

Isosbestic point as referred to herein is a wavelength at which the intensity of absorption of oxyhaemoglobin $HbO_2$ is the same as the intensity of absorption of deoxy-haemoglobin Hb; to such isosbestic points are indicated as $IP_A$ and $IP_B$ in FIG. 10. Similarly, there is an isosbestic range marked IR in FIG. 10 where these two functions are substantially coincident. FIG. 10 is based on Anderson, R. R., Parrish, J. A. (1981) Microvasculature can be selectively damaged using dye lasers: a basic theory and experimental evidence in human skin. Lasers Surg. Med. 1, 263–276.

For monitoring the oxygenation levels of internal organs, fiber-optic blood oximeters have been developed. These fiber-optic devices irradiate the tissue with two wavelengths, and collect the reflected light. By analysis of the reflection intensities at several wavelengths the blood oxygenation is deduced. The wavelengths used in one such system were 585 nm (isosbestic point) and 577 nm (Rampil I. J., Litt L., & Mayevsky A., Journal of Clinical Monitoring, 8, 216–225, 1992). Another blood oximeter measures and analyzes the whole spectrum band 500–620 nm (Kessler M. & Frank K., Quantitative spectroscopy in tissue pp. 61–74. Verlagsgruppe GmbH, Frankfurt au Main, 1992). These devices are relatively complicated and susceptible to interference from ambient light, as well as various electronic and optic drifts. Two light sources are required, and the light sources and the detection system also incorporate optical filters that are interchangeable by mechanical means.

E—Flavoprotein Concentration

In order to determine the metabolic state of various tissues in-vivo it is also possible to monitor the fluorescence of another cellular fluorochrome, namely Flavoproteins (Fp). Referring to FIG. 12, Fp absorbs light at wavelengths of about 400 nm to about 470 nm and fluoresces at wavelengths of about 490 nm to about 580 nm. The Fp level can thus be measured using Fp Fluorometry. The conceptual foundations for Fp Fluorometry were established in the late 1960's and were published in several papers as will be referenced hereinafter. Simultaneous monitoring of NADH and Fp from the same layer or volume of tissue provides better interpretation of the changes in energy production and demand.

Chance et al.(B. Chance, N. Graham, and D. Mayar. A time sharing fluorometer for the readout of intracellular oxidation-reduction states of NADH and Flavoprotein. *The Review of Scientific Instruments* 42 (7):951–957, 1971) used a time-sharing fluorometer to record intracellular redox state of NADH and Fp. They showed a very clear correlation between the two chromophores to changes in $O_2$ supply to the perfused liver. Using a time sharing fluorometer reflectometer simultaneous monitoring of NADH and Fp was performed from the surface of the rat's brain (A. Mayevsky. Brain energy metabolism of the conscious rat exposed to various physiological and pathological situations. *Brain Res.* 113:327–338, 1976). The kinetics of the responses to anoxia or decapitation were identical for the NADH and Fp indicating that the NADH signal comes from the same cellular compartment as the Fp—the mitochondrion.

The five tissue viability parameters described above represent various important biochemical and physiological activities of body tissues. Monitoring them can provide much information regarding the tissues' vitality. For the monitoring of different parameters to have maximum utility however, the information regarding all parameters is required to originate from substantially the same layer of tissue, and preferably the same volume of tissue, otherwise misleading results can be obtained. In general, the more parameters that are monitored from the same tissue volume or layer, the better and more accurate an understanding of the functional state of the tissue that may be obtained.

There are several techniques that relate to the simultaneous in-vivo measuring of multiple parameters in certain tissues, which can be used for the various pathological situations arising in modem medicine.

The prior art teaches a wide variety of apparatuses/devices which monitor various parameters reflecting the viability of the tissue. For example, U.S. Pat. No. 4,703,758 teaches the use of an apparatus for monitoring blood flow by using a light source to emit a beam of light, and a light detector that measures the light received. This provides the value of the intensity of the transmitted light, which inter alia depends upon the blood flow in the path of the light.

U.S. Pat. No. 4,945,896 teaches the use of a multiprobe sensor, using independent microelectrodes implanted inside the brain tissue, for measuring various parameters indicative of the function of the brain. This device includes a laser Doppler flow probe for measuring cerebral blood flow, and a probe for monitoring redox state (NADH). These probes can be mounted sequentially, i.e., one after another in the same housing, or they can be placed side by side. These devices suffer from a major drawback however. Tissue viability is not merely a reflection of various values of parameters measured at different times in one place, or different places at one time. The complex biochemical mechanisms that determine tissue viability are such that short time deviations between measurement at short distances between points of measurement can provide inaccurate or even misleading information. Thus, while the values of blood flow and redox state (NADH) must be monitored simultaneously at the same location, with the monitoring being for the same layer of tissue, this is not performed in the reference.

Another drawback encountered in NADH measurements is the Haemodynamic Artifact. This refers to an artifact in which NADH fluorescence measurements in-vivo are underestimated or overestimated due to the haemoglobin present in blood circulation, which absorbs radiation at the same wavelengths as NADH, and therefore interferes with the ability of the light to reach the NADH molecules. The haemoglobin also partially absorbs the NADH fluorescence. In particular, a reduction of haemoglobin in blood circulation causes an increase in fluorescence, generating a false indication of the true oxidation reduction state of the organ. U.S. Pat. No. 4,449,535 teaches, as means to compensate for this artifact, the monitoring of the concentration of red blood cells, by illuminating at a red wavelength (805 nm) simultaneously and in the same spot as the UV radiation required for NADH excitation and measuring the variation in intensity of the reflected red radiation, as well as the fluorescence at 440–480 nm, the former being representative of the intra-tissue concentration of red blood cells. Similarly Kobayashi et al (Kobayashi S., Nishiki K., Kaede K., Ogata E. J. Appl. Physiol. 31, 93–96, 1971) used ultraviolet (UV) illumination at 366 nm for NADH excitation, and red light at 720 nm for reflection measurements. However, U.S. Pat. No. 4,449,535 has at least two major drawbacks; firstly, and as acknowledged therein, using a single optical fiber to illuminate the organ, as well as to receive emissions therefrom causes interference between the outgoing and incoming signals, and certain solutions with different degrees of effectiveness are proposed. More importantly, though, two different wavelengths are used for illuminating the organ. FIG. 2 (based on Eggert & Blazek, 1987, © the Congress of Neurological Surgeons, Lippincott Williams & Wilkins) illustrates the penetration depth profile for various tissues of the human brain as a function of illuminating radiation wavelength, showing a plateau of relative insensitivity, of penetration depth (PD) with wavelength, for a wavelength range between about 360 nm and about 440 nm. For illuminating wavelengths greater than 440 nm, the penetration depth increases sharply with wavelength. Similar characteristics are found with other organs of the body. Thus, as may be seen from FIG. 2, the use of light radiation at the red end of the spectrum in accordance with U.S. Pat. No. 4,449,535 or as proposed by Kobayashi, to correct for blood haemodynamic artifacts in the NADH signal introduces inaccuracies into the measurements due to differences in penetration depths and therefore in the actual sampling volumes. Even though both radiation wavelengths are incident on the same spot, since detection is also at the same point, effectively two different elements of tissue, volume are being probed since the different radiation wavelengths penetrate the tissue to different depths. This results in measurements that are incompatible one with the other, the blood volume measurement relating to a greater depth of tissue than the NADH measurement. Therefore, the device disclosed by this reference does not enable adequate compensation of NADH to be effected using the simultaneous, though inappropriate, blood volume measurement. There is in fact no recognition of this problem, much less so any disclosure or suggestion of how to solve it. Further, there is no indication of how to measure other parameters such as blood flow rate or blood oxygenation level using the claimed apparatus.

In earlier patents; U.S. Pat. Nos. 5,916,171 and 5,685,313 (which have a common inventor with the present invention), a device is described that enables the monitoring of microcirculatory blood flow (MBF), the mitochondrial redox state (NADH fluorescence) and the microcirculatory blood volume (MBV), using a single source multi-detector electro-optical, fiber-optic probe device for monitoring various tissue characteristics to assess tissue vitality. During monitoring, the device is attached to the fore-mentioned tissue. The probe/tissue configuration enables front-face fluorometry/photometry. The two most important parameters involved in that fiber arrangement are the Optical Penetration Depth (PD) and the Averaged Sample Depth (SD), the PD parameter being dependent on both the tissue-type and on the irradiation wavelength; the SD parameter being dependent on the PD parameter and the distance between the ends of the excitation and collection fiber in contact with tissue.

Although U.S. Pat. No. 5,916,171 and U.S. Pat. No. 5,685,313 represent an improvement over the prior art, they nevertheless have some drawbacks:

(i) The oxidation level of the blood will introduce artifacts, affecting both the Mitochrondrial Redox State measurement (NADH fluorescence) and the microcirculatory blood volume (MBV) since these patents do not specify how to compensate for the oxygenation state of the blood in the tissue, i.e., the relative quantities of oxygenated blood to deoxygenated blood in the tissue. This problem is substantially overcome in the present invention by performing the NADH and blood volume measurements at an isosbestic point of the oxyhaemoglobin deoxyhaemoglobin absorption spectrum.

(ii) There is no facility included for measurement of the oxyhaemoglobin—deoxyhaemoglobin level, i.e. the Blood Oxygenation State, which is also an important tissue viability parameter, worthy of monitoring.

(iii) In these two U.S. patents, the same tissue volume needs to be monitored for all parameters, and the same light source and wavelength is used for the illumination needed for monitoring all three parameters. To measure both the NADH level and the blood flow rate, a relatively powerful UV laser is used. Using a relatively high intensity UV laser illumination source as proposed raises safety issues, especially for long-term monitoring.

(iv) The blood flow measurements impose several requirements on the UV laser source. In particular, the UV laser should have a high coherence length and very low intensity optical noise. Such lasers at these wavelengths are also not standard components and are indeed quite difficult to come by, which might lead to supply problems.

(v) There is no suggestion of monitoring Fp level, with or without any of the other parameters.

It is an aim of the present invention to overcome the above deficiencies in the prior art.

Particularly, it is an aim of the present invention to provide a method and apparatus enabling the simultaneous in-vivo monitoring of blood flow rate (i.e. intravascular mean velocity times the number of moving red blood cells) and at least one, and preferably all, of the following: NADH concentration by fluorescence, total blood volume (i.e. concentration of red blood corpuscles) by reflectometry, blood haemoglobin oxygenation (i.e. the oxy/deoxy haemoglobin ratio) by fluorescence, flavoprotein concentration by fluorescence; for the same body tissue, in substantially the same layer within the same region. These parameters, which represent different biochemical and physiological activities of the tissue, are used to assess the tissue vitality in said layer and tissue region.

It is another aim of the invention to provide flexibility in design of apparatus for simultaneous measurement of four or five different parameters with reference to the same tissue layer.

It is another objective of the present invention to provide a method and apparatus for enabling the blood oxygenation of a tissue to be measured, which overcomes the deficiencies of the prior art.

It is another aim of the present invention to provide a method and apparatus for enabling the blood oxygenation of a tissue to be measured where prior art absorption methods cannot be used.

It is a further aim of this invention to enable the concurrent monitoring of blood parameters in different regions of the same organ.

It is a further aim of this invention to enable the concurrent monitoring of blood parameters in the same or different region of a number of different organs of the same type, for example the kidney of a number of patients.

It is a further aim of this invention to enable the concurrent monitoring of blood parameters in different organs belonging to the same or different patients.

Other objects and advantages of the invention will become apparent as the description proceeds.

These and other objectives are realised by the present invention by a revolutionary approach to tissue viability measurement, directed at a common tissue layer concept rather than based on necessarily using the same excitation wavelength for all parameters. The same tissue layer measurements can be achieved, as explained further on, by-utilizing several wavelengths that are all confined within a well defined wave-band, or alternatively by using even very different wavelengths and making adequate compensation for variable penetration depths, rather than being restricted to using a single radiation illumination as taught by U.S. Pat. No. 5,916,171 and U.S. Pat. No. 5,685,313.

Thus, the NADH fluorescence, blood volume and blood haemoglobin oxygenation state are measured using the same monochromatic illumination wavelength and the same detection fibers, ensuring that the same tissue volume is monitored for these three blood parameters. The illumination point is not coincident with the detection point, and the spacing between these points may be chosen according to the average sample depth that is desired.

The wavelength of the monochromatic light is chosen to lie at one of the isosbestic points of the extinction coefficient vs. wavelength curves for oxyhaemoglobin and deoxyhaemoglobin; wherein the NADH or blood volume measurements will be substantially unaffected by the oxygenation state of the blood.

The blood flow rate may be measured by Laser Doppler Flowmetry (LDF), typically using coherent light (a laser radiation), the illumination being applied at the same point on the tissue as for the above three parameters. Furthermore, this laser radiation can also be used for excitation of Fp fluorescence which enables the monitoring of flavoprotein concentration, which is an important physiological parameter, as discussed above.

However, the location of the detection fibers with respect to the illumination fibers, specifically the distance between their ends, is set to a different value to compensate for the different penetration depth of the two illuminating wavelengths, and thus to ensure that the same layer of tissue is monitored for the blood flow parameter and flavoprotein fluorescence, as is monitored for the other blood and tissue parameters. This distance will vary; both as a function of the tissue type being monitored and as a function of the selected wavelengths of the two illuminations. While it is generally preferable to monitor NADH and LDF over exactly the same tissue volume, not just layer, to achieve this aim, the excitation wavelengths used for the parameters being monitored should be confined within predefined wave-band for which penetration depth is substantially insensitive to wavelength.

Nonetheless, for any given type of tissue, there exists in general, a range of wavelengths with substantially the same penetration depth for each tissue type. For example, as illustrated in FIG. 2 for brain tissues, this plateau in penetration depth as a function of wavelength, extends from about 360 nm to about 440 nm, with some indication from other sources, that the plateau extends to even lower wavelengths. Similarly some other tissues feature similar plateaus at these or other wavelengths. If the monitored tissue is radiated using different wavelengths over the appropriate range, the penetration depth will be similar, and substantially the same volume of tissue may be monitored. In such cases, the same detection fibers may be used for both illuminating wavelengths.

Thus, the present invention also provides a method and apparatus for the measurement of blood oxygenation level based on fluorescence measurements, rather than reflection measurements. Essentially, a single radiation at a particular wavelength illuminates a tissue such as to stimulate the emission of fluorescence by the tissue. The intensity of the fluorescent radiation at two or more wavelengths (within the fluorescent radiation band) is measured, and the level of oxygenation is derived from these measurements. Such a method and apparatus is advantageously incorporated within the apparatus of the invention in which a number of tissue viability parameters are determined. Alternatively, a stand-alone device and corresponding method may be provided for the measurement of blood oxygenation level.

As discussed above, U.S. Pat. No. 5,916,171 and U.S. Pat. No. 5,685,313 are directed at the use of a single radiation at a single wavelength for monitoring a number of tissue viability parameters, including blood flow rate and NADH level. On the other hand, EP 442011 describes a sensor for non-invasive measurement of a single parameter, oxygen saturation in a tissue. In one embodiment, shown in FIG. 2 thereof, a carrier means has mounted therein a single light transmitter emitting electromagnetic waves of different wavelengths, and two receivers at different distances from the transmitter, each receiver being sensitive to a different one of these wavelengths reflected from the tissue.

Returning, to the references U.S. Pat. No. 5,916,171 and U.S. Pat. No. 5,685,313, a single optical fiber guide carries the single illuminating radiation to the tissue and receives light from the tissue via another fiber, and the received light is then directed into two separate channels. A single illuminating radiation is used to ensure that the same tissue volume is being considered for all the tissue vitality parameter measurements. Thus, not only would there be no motivation for a man of the art to consider these documents when desiring to provide an apparatus with two illuminating radiations at different wavelengths, these references actually teach against using more than one illuminating radiation source, and more so at different illuminating wavelengths. On the other hand, EP 422011 is directed exclusively at the measurement of a single parameter, oxygen saturation in a tissue, and does not consider in any shape or form the measurement of multiple tissue viability parameters such as blood flow rate and NADH—in fact it is not concerned with the measurement of two or more parameters, but rather uses both receivers to measure a single parameter. Thus, there would be no motivation for a man of the art to combine EP 442011 with U.S. Pat. No. 5,916,171 or U.S. Pat. No. 5,685,313 when seeking to provide a device according to the present invention. Moreover, even if the sensor of EP 442011 were to be combined with the apparatus of U.S. Pat. 5,916,171 or U.S. Pat. No. 5,685,313, the combination would not yield the present invention. For example, the apparatus of U.S. Pat. No. 5,916,171 and U.S. Pat. No. 5,685,313 does not provide radiation at a range of wavelengths, and the radiation is provided directly from a remote radiation source via optical fiber. This enables a relatively small tissue area to be monitored as the cross-section of the probe can therefore be quite small. On the other hand the sensor of EP 442011 has the transmitter itself (in the form of an LED) mounted onto the carrier, which therefore needs to be large enough to accommodate the same, and which has power leads, rather than optical fibers connecting the carrier to an external power source. Thus, these two devices—the apparatus and the sensor—are not compatible with each other, and very significant modifications to the two would be required to enable the sensor of EP 422011 to be incorporated into the apparatus of U.S. Pat. No. 5,916,171 and U.S. Pat. No. 5,685,313. This still leaves the question of how to configure the combination so that each of the receivers of EP 422011 is coupled to a different measuring channel of the apparatus of U.S. Pat. No. 5,916,171 and U.S. Pat. No. 5,685,313. More importantly, though, the sensor of EP 422011 is characterised in that the two receivers are mounted on the carrier in distances selected such that the lengths of the light paths through the tissue at the two different wavelengths are substantially equal. In such a case, by definition, the two different wavelengths must be directed to two different tissue layers, not to mention entirely different tissue volumes. Thus, not only would the fact that different tissue volumes are targeted by EP 422011 teach away from considering this reference in combination with U.S. Pat. No. 5,916,171 and U.S. Pat. No. 5,685,313 in the first place, such a combination still does not provide the apparatus of the present invention in which a single tissue layer is targeted by both radiations. In the present invention, the relative location of the detection fibers with respect to the illumination fibers, specifically the distance between their ends, is set to such as to compensate for the different penetration depths of the two illuminating wavelengths, and thus to ensure that the same layer of tissue is monitored for the blood flow parameter, as is monitored for the other blood and tissue parameters. Clearly, far from providing this arrangement, EP 422011 teaches away therefrom.

Regarding the determination of oxygenation level of a tissue according to the present invention, such a method and corresponding device are not disclosed or suggested in the prior art.

For example, WO 99/02956 uses a laser induced fluorescence method for assessing the levels of ischemia and hypoxia in a tissue, rather than blood oxygenation level. The method comprises the steps of (a) measuring the fluorescence spectra at two different points on the tissue; (b) calculating the tissue absorption spectrum from these measurements; and (c) calculating the intrinsic fluorescence spectrum. Thus, in order to perform the calculations for determining the absorption spectra, two different points on the tissue need to be considered, and thus the device requires two different detectors coupled to two corresponding measurement channels, in contrast to the present invention in which a single point on the tissue suffices for obtaining fluorescence measurements therefrom, which are in the form of intensity measurements. Further, there is no disclosure or suggestion of using the intensity of the fluorescent radiating at two or more wavelengths for determining ischemia or hypoxia, and less so for determining blood oxygenation level.

In U.S. Pat. No. 5,318,022 and in WO 98/44839, oximetry techniques are described, wherein in each case an excitation source of several wavelengths is used, and the intensity of the reflected radiation for each wavelength is measured, wherein the appropriate ratios of oxygen saturation are determined. In contrast, the present invention uses only a single wavelength, and the intensity of the fluorescent radiation emitted as a result thereof is measured at two or more fluorescent wavelengths, from which blood oxygenation level is determined.

SUMMARY OF THE INVENTION

The present invention relates to an apparatus for selectively monitoring a blood flow rate tissue viability parameter and at least one second tissue viability parameter corresponding to at least a substantially identical layer of tissue element, the apparatus comprising:

illumination means for illuminating at least said layer of tissue element with a first illuminating radiation at a first wavelength and with a second illuminating radiation at a second wavelength via at least one common illumination location with respect to said tissue element;

first radiation receiving means for receiving a first radiation from said layer of tissue element as a result of an interaction between said first illuminating radiation and said layer of tissue element, said first radiation being correlated to said blood flow rate tissue viability parameter, said first radiation receiving means being displaced from said illumination location by a first displacement;

second radiation receiving means for receiving at least a second radiation from said layer of tissue element as a result of an interaction between said second illuminating radiation and said layer of tissue element, said second radiation being correlated to said at least one second tissue viability parameter, said second radiation receiving means being displaced from said illumination location by a second displacement.

Typically, the blood flow rate tissue viability parameter is provided by the Doppler shift of said first radiation received by said first radiation receiving means with respect to the said first illuminating radiation. First detection means are provided for detecting said first radiation received by said first radiation receiving means.

The second tissue viability parameter may be NADH concentration, and said corresponding second radiation received by said second radiation receiving means is an NADH fluorescence emitted by the tissue in response to illumination thereof by said second illuminating radiation, said at least one second tissue viability parameter being provided by the intensity of said NADH fluorescence. Second detection means are provided for detecting said second radiation received by said second radiation receiving means.

Additionally or alternatively, the second tissue viability parameter is blood volume within said tissue element, and said corresponding second radiation received by said second radiation receiving means is a reflection from the tissue element in response to illumination thereof by said second illuminating radiation; the said at least one second tissue viability parameter being provided by the intensity of said reflection. Third detection means for detecting said second radiation received by said second radiation receiving means.

Additionally or alternatively, the second tissue viability parameter is blood oxygenation ratio within said tissue element, and said corresponding second radiation received by said second radiation receiving means is a fluorescence emitted by the tissue in response to illumination thereof by said second illuminating radiation, said at least one second tissue viability parameter being provided by the intensity of said fluorescence at least at two fluorescent wavelengths. Optionally, one of said at least two fluorescent wavelengths is chosen to lie at an oxy-deoxy fluorescence emission isosbestic point. Alternatively, one of said at least two fluorescent wavelengths is higher and another one of said at least two fluorescent wavelengths is smaller than a wavelength corresponding to an oxy-deoxy fluorescence emission isosbestic point. Fourth detection means for detecting said second radiation received by said second radiation receiving means.

The common illumination location is typically provided by at least one excitation optical fiber capable of being brought into registry with said tissue element. The ratio of said first displacement to said second displacement may be substantially correlated to a ratio of said second wavelength to said first wavelength. In one embodiment, the first radiation receiving means comprises at least one suitable first receiving optical fiber capable of being brought into registry with said tissue element, and the second radiation receiving means comprises at least one suitable second receiving optical fiber capable of being brought into registry with said tissue element. Preferably, the at least one excitation optical fiber, said at least one first receiving optical fiber and said at least one second receiving optical fiber are housed in a suitable probe head.

In another embodiment, the ratio of said first displacement to said second displacement is substantially unity. Optionally, but not necessarily, the first wavelength is substantially the same as said second wavelength, and the first wavelength and said second wavelength have substantially similar penetration depths with respect to said tissue element. In this embodiment, the first radiation receiving means and said second radiation receiving means are comprised of at least one common third optical fiber capable of being brought into registry with said tissue element. Preferably, the at least one excitation optical fiber and said at least one common third optical fiber are housed in a suitable probe head.

For all embodiments, the first illuminating radiation of said first wavelength is typically provided by a first coherent light source, which is preferably a laser light source. Optionally, the laser light source is adapted to provide said first illuminating radiation of said first wavelength in pulses of predetermined duration and intensity. Optionally, the apparatus may further comprise suitable control means for controlling the frequency of pulsing of said pulses. The control means may be further adapted to provide said pulses in packages of pulses, each package comprising at least one pulse and separated from a preceding or following package by a predetermined time period. This predetermined time period is greater than the time interval between consecutive pulses within a package. Preferably, this time period is controllably variable, and the number of pulses within each package is also controllably variable. Advantageously, the control means is operatively connected to at least one of said first detection means, second detection means, said third detection means and fourth detection means. The control means is preferably selectively responsive to previously detected signals corresponding to the detection of said second radiation detected by means of any one of said second detection means, said third detection means or said fourth detection means, of a prior monitoring cycle.

For all embodiments, the said second wavelength is chosen to lie at a suitable isosbestic point of the NADH. This isosbestic point is within a substantially isosbestic range of the oxyhaemaglobin—deoxyhaemaglobin absorption vs. wavelength curves. Typically, the said second wavelength is within the range of wavelengths corresponding to the NADH excitation spectrum, and is typically between about 300 nm and about 395 nm, and preferably between about 300 nm and about 340 nm. More specifically, the said second wavelength is within about ±5 nm of any of the following wavelengths; 325 nm, 337 nm, 349 nm, 355 nm, 366 nm, 370 nm, 385 nm or 390 nm. The radiation of said second wavelength may be provided by any suitable UV light source.

In some embodiments such as in the first embodiment, the first wavelength may be substantially different from said second wavelength. In other embodiments, such as in the second embodiment, the first wavelength may be substantially similar to or even the same as the second wavelength, wherein the penetration depths associated with the first and second wavelengths are substantially the same.

In the first embodiment, the first wavelength is typically about 440 nm or greater than this. In the second embodiment, the first wavelength is typically between about 300 nm and about 440 nm.

Typically, then, the first wavelength may be either in the range 410±30 nm or within about ±5 nm of any one of the following wavelengths; 355 nm, 430 nm, 440 nm, 455 nm, 460 nm, 490 nm, 532 nm or 805 nm.

In the third and fourth embodiments of the invention, the apparatus is adapted for further monitoring a flavoprotein concentration tissue vitality parameter, comprising fifth detection means for detecting a portion of said first radiation received by said first radiation receiving means, said portion of said received first radiation being a flavoprotein fluorescence emitted by the said tissue element in response to illumination thereof by said first illuminating radiation, said flavoprotein tissue viability parameter being provided by the intensity of said flavoprotein fluorescence. In these embodiments, the said first wavelength is within the range of wavelengths corresponding to the flavoprotein excitation spectrum. Typically, the first wavelength is between about 400 nm and about 470 nm, and preferably within about 440 nm and 460 nm.

The present invention also relates to a system for selectively monitoring at least two tissue viability parameters at a plurality of tissue elements; said system comprising a plurality of monitoring probes, each said probe comprising an apparatus as described hereinbefore. At least two said probes may be adapted for monitoring said tissue viability parameters of tissue elements within the same organ. Additionally or alternatively, at least two said probes are adapted for monitoring said tissue viability parameters of tissue elements within different organs. The different organs may be different organs within the same organism, and/or different organs within different organisms, and/or include donor organs.

The second illuminating radiation of said second wavelength for each said probe may be provided by a common suitable light source, which is typically a UV monochromatic light source or the like, which in turn may be adapted to provide said second illuminating radiation of said second wavelength in pulses of predetermined duration and intensity. The system optionally further comprises suitable control means for controlling the frequency of pulsing of said pulses.

Similarly, the first illuminating radiation of said first wavelength for each said probe may be provided by a common suitable light source, which is typically a laser light source, which in turn may be adapted to provide said first illuminating radiation of said first wavelength in pulses of predetermined duration and intensity. The system optionally further comprises suitable control means for controlling the frequency of pulsing of said pulses. The control means may be further adapted to provide said pulses in packages of pulses, each package comprising at least one pulse and separated from a preceding or following package by a predetermined time period. The predetermined time period may be set to be greater than the time interval between consecutive pulses within a package. Preferably, this time period is controllably variable. The number of pulses within each package may also be controllably variable. The control means may be adapted for selectively directing discrete said pulses to any one of said probes.

The system optionally further comprises any one and preferably all of the following:
(a) suitable first common detection means for detecting said first radiation received by said first radiation receiving means of at least two said probes, and coupling means for optically connecting the at least two said probes to said first common detection means;
(b) suitable second common detection means for detecting said second radiation received by said second radiation receiving means of at least two said probes, and coupling means for optically connecting the at least two said probes to said second common detection means, wherein said second tissue viability parameter corresponding to said second radiation is NADH concentration;
(c) suitable third common detection means for detecting said second radiation received by said second radiation receiving means of at least two said probes, and coupling means for optically connecting the at least two said probes to said third common detection means, wherein said second tissue viability parameter corresponding to said second radiation is blood volume;
(d) suitable fourth common detection means for detecting said second radiation received by said second radiation receiving means of at least two said probes, and coupling means for optically connecting the at least two said probes to said fourth common detection means, wherein said second tissue viability parameter corresponding to said second radiation is blood oxygenation ratio;
(e) suitable fifth common detection means for detecting a portion of said first radiation received by said first radiation receiving means of at least two said probes, said portion of said received first radiation being a flavoprotein fluorescence emitted by the said tissue element in response to illumination thereof by said first illuminating radiation, said flavoprotein tissue viability parameter being provided by the intensity of said flavoprotein fluorescence, said system further comprising coupling means for optically connecting the at least two said probes to said fifth common detection means.

The control means may be operatively connected to the first common detection means. Optionally, the control means may also be operatively connected to any one of, and preferably all of, the first common detection means, the second common detection means, the third common detection means, the fourth common detection means and the fifth common detection means.

The control means may also be selectively responsive to previously detected signals corresponding to the detection of said second radiation detected by means said second, third, fourth or fifth common detection means of a prior monitoring cycle, respectively.

In a another aspect of the invention, the present invention is directed to a method for determining the oxygenation state of a tissue element, comprising:
providing an illuminating radiation to the tissue element, said illuminating radiation being at a wavelength within the NADH excitation spectrum or within the flavoprotein (Fp) excitation spectrum;
measuring the intensity of the corresponding NADH or Fp fluorescence, respectively, emitted by the tissue element at least at two predetermined wavelengths within the range of wavelengths comprised in the corresponding fluorescence emission;
comparing the intensities measured in (b) to provide an estimate of the relative levels of oxygenated blood to deoxygenated blood in said tissue element.

One of said wavelengths in the second step may be chosen to lie at a suitable second isosbestic point, which is a suitable NADH oxy-deoxy fluorescence emission isosbestic point, or an Fp oxy-deoxy fluorescence emission isosbestic point, respectively.

The intensity of fluorescence emitted by the tissue element at two target wavelengths within the range of wavelengths comprised in the fluorescence may be measured, wherein a first target wavelength thereof is chosen at below the wavelength corresponding to said second isosbestic point, and wherein a second said target wavelength thereof is chosen at above the wavelength corresponding to said second isosbestic point. Preferably, the first target wavelength and the second target wavelength are chosen such as to correspond to the maximal change in fluorescence intensity occurring at wavelengths below and above, respectively, the second isosbestic point.

The intensity of fluorescence emitted by the tissue element may be measured over a range of wavelengths within a specified window of the range of wavelengths comprised in the fluorescence.

In the third step of the method, the fluorescence intensity at each wavelength in the second step is normalised by a "normalising" fluorescence intensity measured at a suitable corresponding NADH OR Fp oxy-deoxy fluorescence emission isosbestic wavelength within the corresponding fluorescence emission spectrum.

The method may be adapted for NADH, wherein the illuminating radiation in step (a) is within the range of wavelengths comprised in the NADH excitation spectrum, and in which case the "normalising" fluorescence intensity is measured at an isosbestic wavelength of about 455 nm±5 nm.

Alternatively, the method may be adapted for Fp, wherein the illuminating radiation in step (a) is within the range of wavelengths comprised in the Fp excitation spectrum, and in which case the "normalising" fluorescence intensity is measured at an isosbestic wavelength of about 530 nm±5 nm.

The illuminating radiation is typically, but not necessarily provided at a suitable NADH oxy-deoxy fluorescence excitation isosbestic wavelength or a Fp oxy-deoxy fluorescence excitation isosbestic wavelength, respectively, within the corresponding NADH or Fp fluorescence excitation spectra, respectively.

According to this aspect of the invention, an apparatus is provided for determining the oxygenation-state of a tissue element, comprising:
illumination means for illuminating said tissue element with an illuminating radiation at a predetermined wavelength via at least one illumination location with respect to said tissue element;
radiation receiving means for receiving a fluorescence emitted from said tissue element as a result of an interaction between said illuminating radiation and said tissue element,
suitable detection means for detecting said fluorescence received by said radiation receiving means.

The detection means is adapted for detecting the intensity of the fluorescence received by said radiation receiving means at least at two fluorescent wavelengths. One of said at least two fluorescent wavelengths may be chosen to lie at an isosbestic point in the fluorescent emission spectrum.

Alternatively, one of said at least two fluorescent wavelengths is higher and another one of said at least two fluorescent wavelengths is smaller than a wavelength corresponding to an isosbestic point in the fluorescent emission spectrum. Preferably, the said predetermined wavelength of said illuminating radiation corresponds to an isosbestic point of the excitation spectrum. The illumination location is typically provided by at least one excitation optical fiber capable of being brought into registry with said tissue element. The radiation receiving means typically comprises at least one suitable first receiving optical fiber capable of being brought into registry with said tissue element. The at least one excitation optical fiber and the at least one receiving optical fiber are preferably housed in a suitable probe head. Typically, the predetermined wavelength of said illuminating radiation is within the range of wavelengths corresponding to the NADH excitation spectrum, and the fluorescence emitted from said tissue as a result of an interaction between said illuminating radiation and said tissue element is an NADH fluorescence emission. Alternatively, the predetermined wavelength of said illuminating radiation is within the range of wavelengths corresponding to the Fp excitation spectrum, and the fluorescence emitted from said tissue as a result of an interaction between said illuminating radiation and said tissue element is an Fp fluorescence emission.

Thus the present invention relates to an apparatus or device for in-vivo monitoring of NADH level, Fp level, microcirculatory blood volume, microcirculatory blood flow and blood haemoglobin oxygenation, in the same layer of tissue in substantially the same location over the same time period, and corresponding methods for performing said monitoring.

More particularly, the invention relates to a single probe device that measures these parameters, indicative of the function of the tissue in the identical layer and substantially the same location of the tissue; determining the ratios of those parameters, and storing and retrieving said information to enable long-term monitoring.

The NADH level, microcirculatory blood volume and blood haemoglobin oxygenation being determined by monitoring the fluorescence and reflectance resulting from UV monochromatic light irradiation at an isosbestic wavelength of the oxy-deoxy haemoglobin absorption spectrum. The microcirculatory blood flow and Fp level being measured by Laser Doppler Flowmetry (LDF), with irradiation by a suitable laser light source.

The present invention enables the monitoring of the metabolic state of a tissue by NADH fluorometry. Using the device of the invention, it is possible to monitor NADH levels in a certain tissue volume and to correct efficiently for the Haemodynamic Artifact. Reflection measurements are used to monitor the blood volume that present in the same volume element, and to resolve the interference of haemoglobin with the NADH measurements. The reflection measurements are taken at the same wavelength, and from the same tissue sample as the NADH measurements. This enables monitoring of corrected NADH fluorescence in same volume element. All fluorescence excitation measurements are performed at low irradiation intensities to avoid photo-bleaching of the measured NADH chromophores. In addition, NADH excitation wavelengths are specified to resemble the isosbestic points of the Haemoglobin oxy-deoxy absorption spectrum. This prevents artifact resulting from the changes in the oxygenation state.

The reflection of the light at the excitation wavelength is used to monitor the Blood Volume in same volume element examined. The reflection signal is measured in the excitation wavelength, which is at an isosbestic point of the absorption spectra of oxyhaemoglobin and deoxyhaemoglobin and at NADH excitation wavelengths. The irradiation intensity is maintained as low as possible in order to eliminate possibility of photo-damage to the irradiated tissue.

The blood flow rate is monitored using Laser Doppler Flowmetry. The light intensity is optimized to give a high signal-to-noise ratio, with the choice of wavelength and intensity being specified to minimise the possibility of photo-damage to the irradiated tissue. The laser irradiation signal is modulated by suitable chopping means to limit the exposure of the tissue to laser light to within acceptable limits. By utilizing a separate light source for monitoring the blood flow from that used for monitoring the other parameters, it is possible to monitor the other parameters constantly over extended periods of time whilst only irradiating the tissue with the laser light required for measuring the blood flow on an intermittent basis. The LDF system can be activated periodically by a clock triggering mechanism, or it may also be switched to actively monitor the volume blood flow during periods of activity, being triggered by a change in one of the other parameters.

BRIEF DESCRIPTION OF THE DRAWINGS

The present invention will be more clearly understood from the detailed description of the preferred embodiments and from the attached drawings in which:

FIG. 3($b$) shows in greater detail the tissue-abutting end of the probe of FIG. 3($a$).

FIG. 4($b$) illustrates in end view a second embodiment of the probe of the present invention.

FIG. 6($b$) illustrates schematically the ratio of fluorescence intensities at two wavelengths with respect to the fluorescence intensity at an isosbestic point of FIG. 6($a$).

FIG. 7($a$) shows the main clock sequence that enables the transmission of the light from light source (102) by the acousto-optic modulator (AOM).

FIG. 7($b$) shows the output voltage of the detector in response to the light modulated by the AOM.

FIG. 7($c$) shows the clock sequence applied to the sample and hold (S/H) circuitry (440) and (470) as shown in FIGS. 9($a$) to 9($c$).

FIG. 7(d) shows the clock sequence that is applied to the reference sample and hold (S/H) circuitry (450) as shown in FIGS. 9(a) to 9(c).

FIG. 7(e) shows the light signal as it appears at the output of (S/H) circuitry (450) and (470) of FIGS. 9(a) to 9(c).

FIG. 7(f) shows the sequence train of pulses as provided during state II operation of the device.

FIG. 7(g) shows the sequence train of pulses as provided during state III operation of the device.

DETAILED DESCRIPTION OF PREFERRED EMBODIMENTS

The present invention is defined by the claims, the contents of which are to be read as included within the disclosure of the specification, and will now be described by way of example with reference to the accompanying figures.

In the description to follow, the following illustrative apparatuses and methods are described, it being understood that the invention is not limited to any particular form thereof, and the following description being provided only for the purposes of illustration.

The present invention is directed to an apparatus for simultaneously monitoring at least one tissue viability parameter from each of two sets of tissue viability parameters, from at least a substantially identical layer of tissue element, and preferably from the same volume of tissue, element. In particular, one of these parameters of the first set is the blood flow rate corresponding to the tissue layer, and a dedicated radiation at a particular wavelength is used for monitoring this parameter in conjunction with a laser Doppler flowmetry method (LDF). The second set of tissue viability parameters includes at least one of, and preferably more than one of, and most preferably all of, at least NADH concentration, blood volume, blood oxygenation corresponding to the tissue layer, and this parameter or plurality of parameters are measured using another dedicated radiation at a desired wavelength, which may be chosen to be the same as or different from the wavelength of the radiation used for monitoring the blood flow rate. The first set of tissue viability parameters also includes a fifth tissue viability parameter, flavoprotein concentration, can be monitored using the same illumination source that is used for the LDF measurements.

Thus—this being a great advantage of the present invention—the blood flow rate measurement is conducted totally independently from the monitoring of the second set of tissue viability parameters, providing a great deal of flexibility in terms of configuration and design of the monitoring apparatus, as well as in the method of use, as will be evident from the following description.

Figure 1:
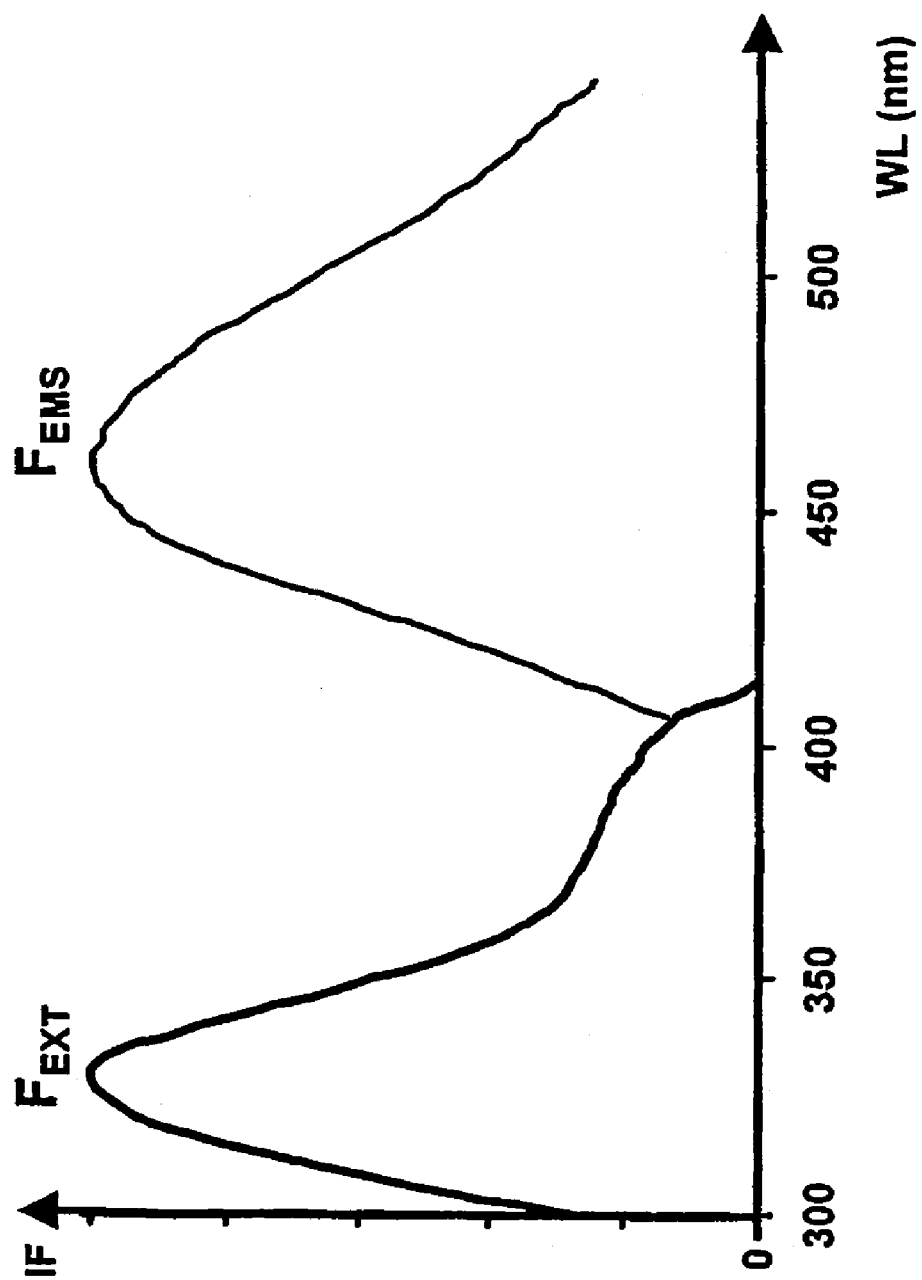
FIG. 1 shows the excitation fluorescence spectrum ($F_{EXT}$) and emission fluorescence spectrum ($F_{EMS}$) for NADH in terms of the corresponding fluoresence intensities (IF) as a function of wavelength (WL).

The wavelength of the illumination radiation that is required for any of the second set of blood viability parameters—NADH, blood volume and oxy-deoxy state—is determined by the absorption and fluorescence characteristics of the NADH in the tissue, as exemplified in FIG. 1 for human brain tissue (the absorption and fluorescence characteristics of NADH are similar for other tissues). The fluorescence wavelength band is typically between about 400 nm and about 550 nm, and an excitation wavelength between about 300 nm and about 400 nm needs to be provided.

Figure 10:
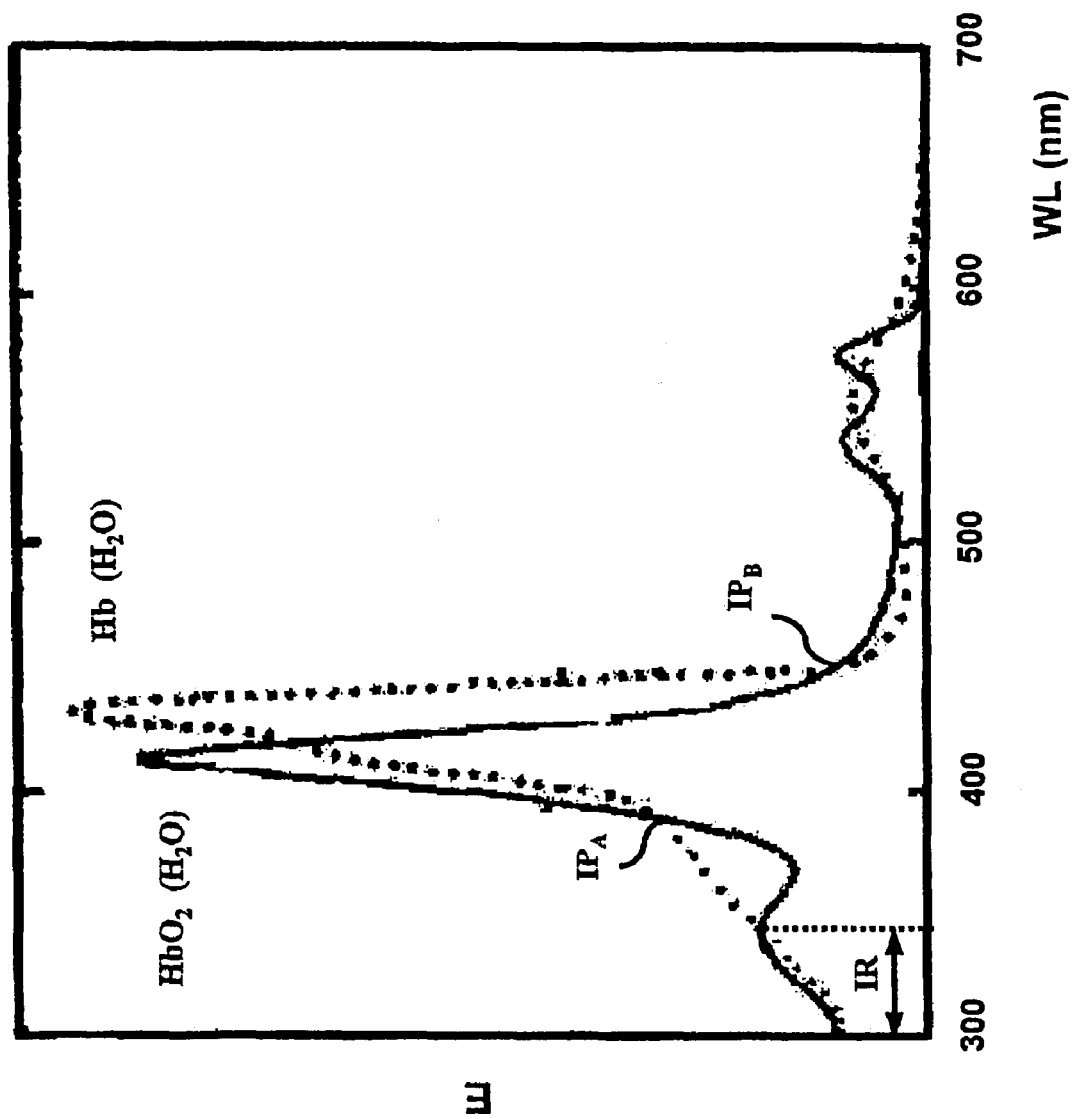
FIG. 10 illustrates light absorption of blood oxy-haemoglobin and blood deoxyhaemoglobin in terms of an Extinction parameter (E) as a function of wavelength (WL).

Preferably, an excitation wavelength is chosen such as to simplify correction for the haemodynamic artifact. The haemodynamic artifact arises from the absorption of the NADH fluorescence emission and excitation light by the blood haemoglobin. A change in blood volume cause misleading changes in apparent NADH fluorescence. Since blood haemoglobin has two oxygenation states namely oxy-haemoglobin and deoxy-haemoglobin each one with its distinct absorption spectrum, as shown in FIG. 10, the precise correction of the haemodynamic effect can become extremely complex. The problem is considerably simplified when the wavelength chosen for NADH fluorescence excitation corresponds to one of the isosbestic points, since at these wavelengths the absorption of both haemoglobin species is identical. At these isosbestic excitation points, fluorescence changes are due substantially to changes in total blood volume, and, of course, to changes in NADH concentration only. Thus, by suitably choosing the excitation wavelength, correction for the haemodynamic artifact is significantly simplified. Even at wavelengths within the isosbestic range of from about 300 nm to about 340 nm, or at the isosbestic point of 390 nm, the haemodynamic artifact requires correction. Suitable algorithms for this purpose are described on the prior art (Koyabashi et al., 1971; Renault G., et al. American Journal of Physiology, 246, H491-H499, 1984; Mayevsky A. and Chance B., Brain Res. 65, 529–533, 1974; Harbig et al., J. Appl. Physiol. 41, 480–488, 1976; U.S. Pat. No. 4,449,535). The most widely used correction algorithm (Jobsis et al. Neurophysiology 3465, 735–749, 1971) utilizes the value of the reflection at the NADH excitation wavelength as an indicator for blood changes. The corrected NADH fluorescence values are calculated by subtraction of the reflection signal from the fluorescence signal.

At the same time, the wavelength of the illumination radiation that is required for the monitoring of the first tissue viability parameter—i.e., the blood flow rate—may be independently chosen from that required for the other parameters. For the various soft body tissues, there are ranges of wavelengths over which the penetration depths of incident light is relatively independent. This is illustrated by way of example for brain tissue in FIG. 2. Here the penetration depth into tissue is relatively independent of the incident radiation wavelength for wavelengths between 360 nm to about 440 nm, while above this range, the penetration depth increases dramatically with wavelength.

The Optical Penetration Depth (PD) may be defined as the depth where the total optical power of incident light is reduced to 37% of the incident power. The PD parameter is useful for estimation of light depth penetration into tissues. If two different wavelengths are used in the same instrument it is important to compare the penetration depth for both wavelengths in order to estimate differences in collected light intensities. In general the PD is proportional to $1/\mu^{1/2}$, where $\mu$ is the total absorption coefficient, given by:

$$\mu = \mu_a + \mu_s$$

where $\mu_a$ is the apparent absorption coefficient due to light absorption; and $\mu_s$ is the apparent absorption coefficient due to light scattering.

The average sample depth (SD) parameter is dependent on the tissue, the wavelength used and on the separation distance of the excitation and collection fibers in the probe. The SD can be approximated by the equation (Taitelbaum H., OSA Proceeding on Advances in Optical Imaging and Photon Migration (ed. by Alfano R. R.) 21, 305–309, 1994):

$$SD \approx 0.4 \cdot r^{1/2} \cdot PD^{1/2}$$

where r is the distance between the excitation and collection fiber. This coefficient depends on both the fiber separation and on the PD.

Apparatuses that incorporate a laser light source are generally required to comply with relevant laser safety standards. The two relevant standards which deal with exposure of human tissue to laser radiation are the ANSI Z136.1-2000 "American National Standard for Safe Use of Lasers" and the IEC60825-1-1994 International Standard called "Safety of laser products".

These standards define the Maximum Permissible Exposure (MPE) values. These standards relate to laser irradiation of external tissues such as skin and eye and not of the internal organs, in contrast to typical applications of the present invention. Still they are the only known, well established references to safe irradiation values for tissues, and any laser device that is intended to perform nondestructive measurements should comply with these in the absence of a more appropriate full damage test being performed on specific tissue type with specific light irradiation.

Both the above standards permit a maximum of 1 mW/cm$^2$ irradiance for the UVA wavelengths region (about 315 nm to about 400 nm) for an exposure time larger then 1000 sec. This requirement implies a severe limitation on the light intensity emitted by the distal tip of the fiber optic probe, particularly when shorter wavelength, higher intensity radiation is used.

In the present specification, the magnitudes of wavelengths specified herein may be varied by about ±5 nm, and even up to about ±10 nm without significantly affecting operation of the apparatus of the invention.

The first embodiment of the present invention, according to a first aspect thereof, is directed to an apparatus in which the wavelength of the illumination radiation that is required for monitoring the first set of tissue viability parameters is outside the range of relative independence of penetration depth with wavelength. By way of example for brain tissue, this illumination would have a wavelength substantially higher than about 440 nm, while the second embodiment of the present invention is directed at an apparatus in which the wavelength of the illumination radiation that is required for the first set of tissue viability parameters is within said range of relative independence, being between 300 nm and about 440 nm if the brain is the tissue under examination. As will become clearer hereinbelow, the question of whether the first set of tissue parameters includes the blood flow rate and flavoprotein fluorescence, or only the blood flow rate, will depend on whether or not the first illuminating radiation is of a wavelength within the flavoprotein excitation spectrum, respectively.

The second aspect of the present invention is directed towards a method and corresponding apparatus for the monitoring of blood oxygenation state using fluorescence measurements. Such method and apparatus may also be advantageously incorporated in the apparatus according to the first aspect of the present invention.

Figure 2:
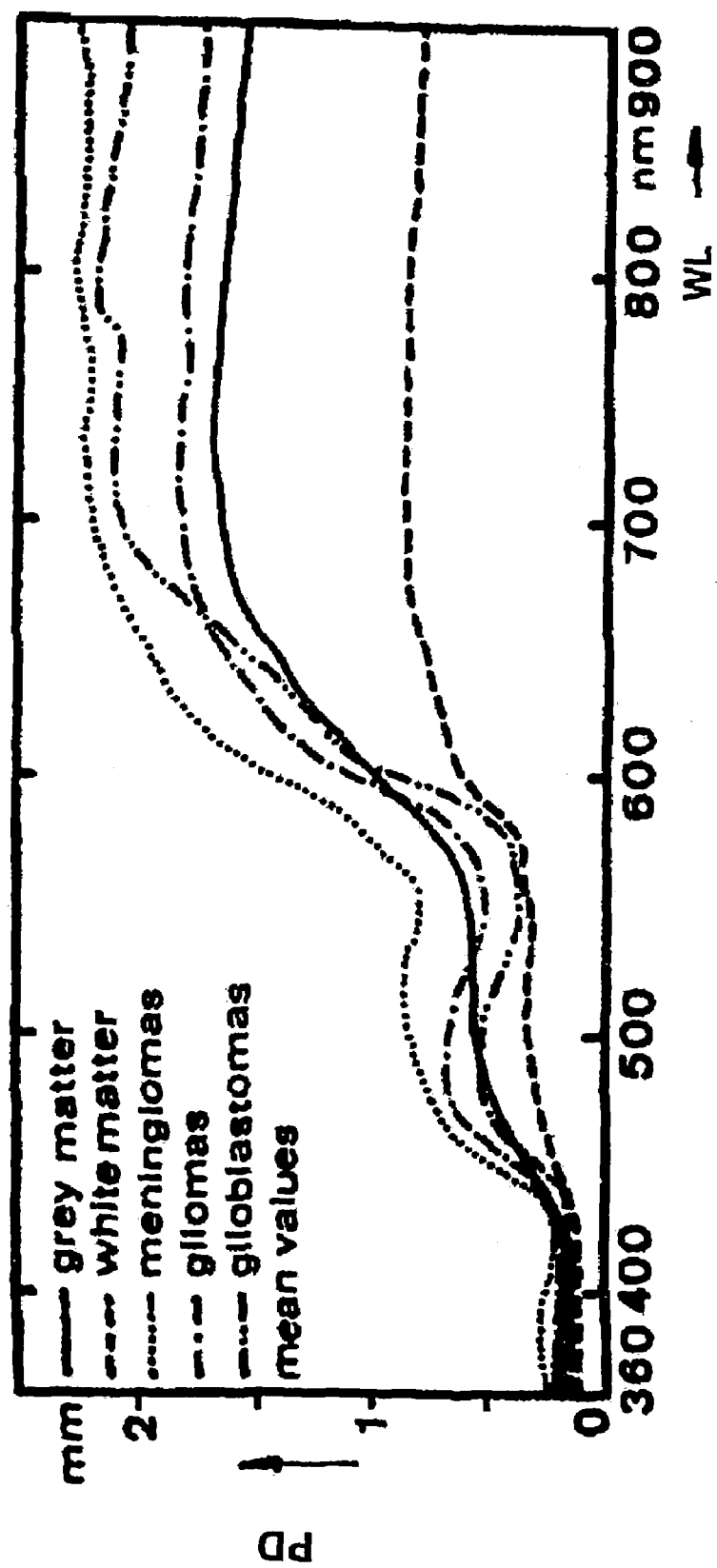
FIG. 2 illustrates typical penetration depth characteristics for human brain tissues as a function of illumination wavelength.
Figure 3B:
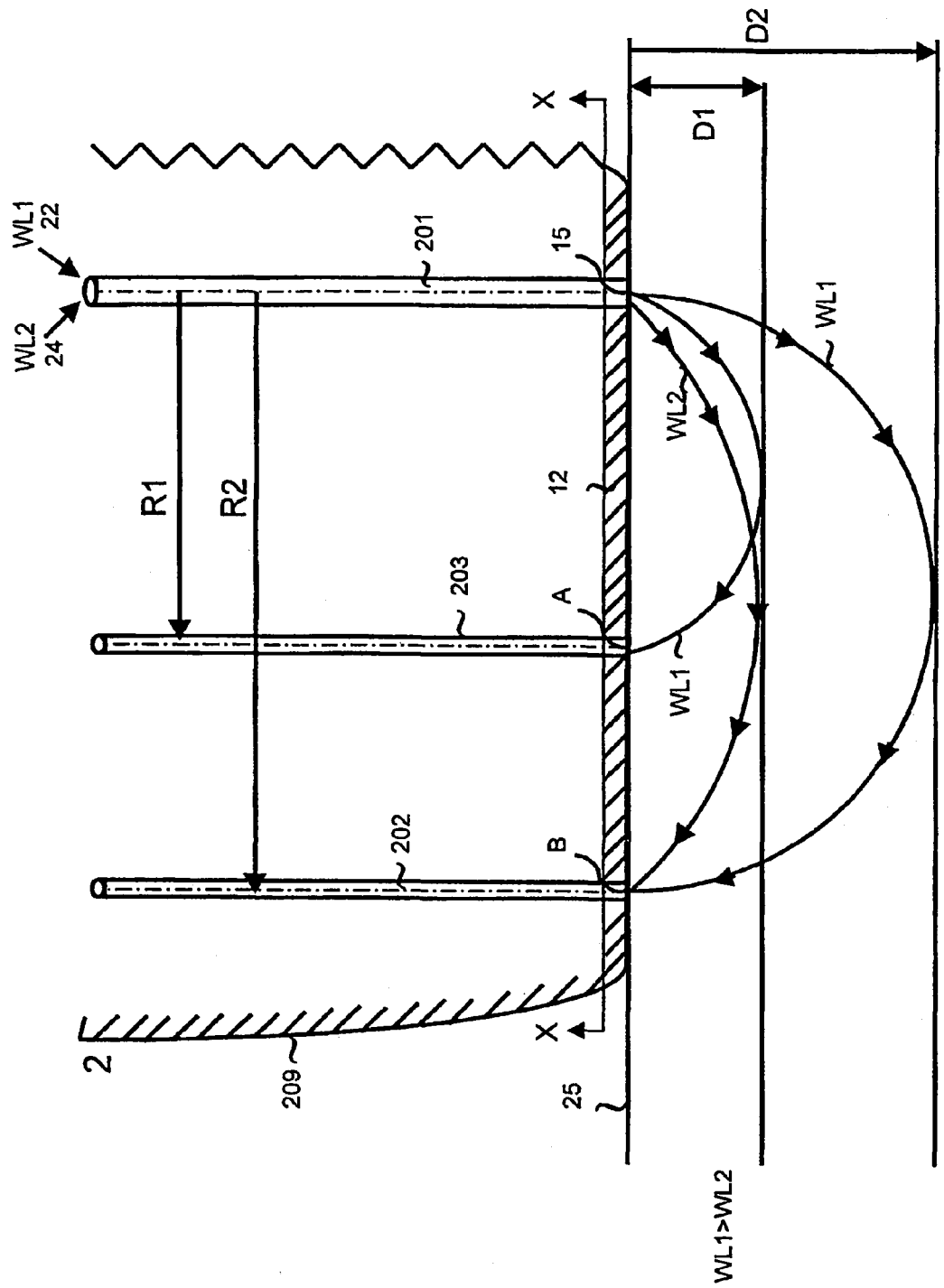
FIG. 3($a$) illustrates, in transverse cross-sectional view, a probe according to a first embodiment of the first aspect of the present invention.

Thus, in the first aspect of the present invention, and referring to FIGS. 3(a), 3(b), 4(a) and 5, the apparatus according to the first embodiment, generally designated by the numeral (100), is directed to the monitoring of blood flow rate of the first set of tissue viability parameters, and any combination of the three tissue viability parameters of the second set of tissue viability parameters. Thus, the apparatus (100) may be in the form of a probe (2) having at the distal tip thereof contact face (12) for making contact with the surface of the tissue (25) being monitored. In its simplest form, the probe (2) has a single fiber (201) for directing two radiations of different wavelengths to the same point (15) on the tissue (25). Alternatively, a bundle of fibers may replace a single fiber (201). The two radiations may come from first and second sources, (22) and (24) respectively, and are coupled to the fiber (201) by any suitable optical coupler. Referring to FIG. 2, other than at the plateau of wavelengths between 300 nm and about 440 nm; for a given illumination wavelength substantially above this range, the further the detection means is displaced from the illumination means, the greater the effective depth into the tissue that may be monitored by the detection means. Thus, if a detection means is provided at location A displaced by a distance R1 from the illumination fiber (201), the radiation from first source (22) having wavelength (WL1) will penetrate to a depth (D1) as illustrated in FIG. 3(b). If the detection means is at position (B), displaced from the illuminating fiber (201) at a greater distance (R2), then the penetration of the radiation corresponding to this position is much greater (D2). When second source (24) provides radiation of wavelength (WL2), substantially shorter than (WL1), if detection is effected from position (B) as well, the data obtained relating to the second source (24) will be for a much shallower depth than for the first source (22). Conversely, if the detection with respect to the higher wavelength (WL1) is performed at a distance, say (R1), closer to the illuminating fiber (201) than the detection distance (R2) with respect to the lower wavelength (WL2), then it is possible to choose (R1) and (R2) such that the detection corresponding to both wavelengths corresponds to the same sampling depth (D1). While the actual sampling volumes for each of the wavelengths in such a case will be different, the quality of results obtained is substantially insensitive to such differences since it confined to the same tissue layer, in contrast to providing results at substantially different depths.

For most body tissues, the anatomic structure of the blood supply is generally similar in that there is a definite gradient in blood oxygenation level with penetration into the tissue. The oxygenated blood supply to the tissue can be in the general direction from the monitored surface into the tissue, as in the brain, or out of the tissue towards the monitored surface as in the skin or the kidneys. In common to both flow directions however, the blood carrying capillaries running parallel to the tissue surface in the superficial layers substantially run randomly throughout the two dimensional plane. Since the overall direction of blood supply is thus generally perpendicular to the tissue surface, the changes in blood flow, blood oxygenation and partial oxygen pressure will occur along the normal to the tissue surface rather than in the plane of the tissue surface. On the other hand, the distribution of cells and mitochondria is very homogeneous along the vertical as well as the horizontal axis in all tissues. Therefore, monitoring of blood flow, oxy-deoxy haemoglobin, NADH fluorescence, as well as flavoprotein fluorescence, will be homogeneous in the plane parallel to the tissue axis, whereas monitoring along an axis perpendicular to the tissue surface will provide heterogeneous results.

Preferably, the probe (2) comprises plastic flexible housing in the form of tube (208) to protect the optical fibers, which are advantageously encapsulated within a stainless steel tube (209) at its distal tip.

As described above, the configuration of the excitation fiber (201) and the collection fibers (202), (203), in particular their relative positions within the probe (2), is important in ensuring that at least the same tissue layer is being considered for all the parameters being monitored. When more than one detection fiber (202) and more than one detection fiber (203) are used, this combined plurality of fibers may be arranged in two sets on concentric circles arranged coaxially with the excitation fiber (201), as illustrated in FIG. 4(a). The gaps or distances (R2), (R1), respectively between the excitation fiber (201) and each set of collection fibers (202), (203) influence both the average sample depth (SD) and the collected signal intensity. The number of collection fibers (202), (203), as well as the core diameters of each type of fiber, also influence both these factors as well as the signal to noise ratio (S/N) of the laser Doppler measurements. For example, good results for monitoring the blood flow in brain gray matter tissues were achieved using a 532 nm laser illumination source, a 200 micron core excitation fiber (201), used together with four collection fibers (203), each of 100 micron core diameter; and a separation gap (R1) of 0.25 mm.

If the second group or set of parameters, (i.e. NADH fluorescence, blood volume and blood oxygenation state) is measured by 390 nm excitation light, for example, the collecting fibers (202) should be placed at a separation gap (R2) three times the separation gap (R1) in order to ensure measurement from the same tissue layer. This requirement originates in the fact that the PD of the 532 nm light is about 0.6 mm for brain gray matter (see FIG. 2) while the PD for the 390 nm light is about 0.2 mm. In other words, at an excitation wavelength of about 390 nm the PD is three times lower than for excitation wavelengths of 532 nm. Since the sampling depth determined by the relationship $SD \approx 0.4 (R*PD)^{1/2}$ it is clear that in order to maintain the same SD for both wavelengths the separation gap (R2) should be three times larger for NADH fluorescence collecting fiber (202). Therefore the fiber (202) should be placed at about 0.75 mm from the excitation fiber (201). The diameter of this collecting fiber (202) may be larger than the diameter of collection fibers (203), since the collected intensity will be lower at such large distance.

For monitoring other body tissues, the gaps (R1), (R2) between the excitation fiber (201) and the collection fibers (203), (202), the number of each of the collection fibers (202), (203) provided in the probe (2), and the core diameters of the excitation fiber (201) and of the collection fibers (202), (203) may be individually optimized for each tissue type and for each type of excitation wavelengths.

Figure 5:
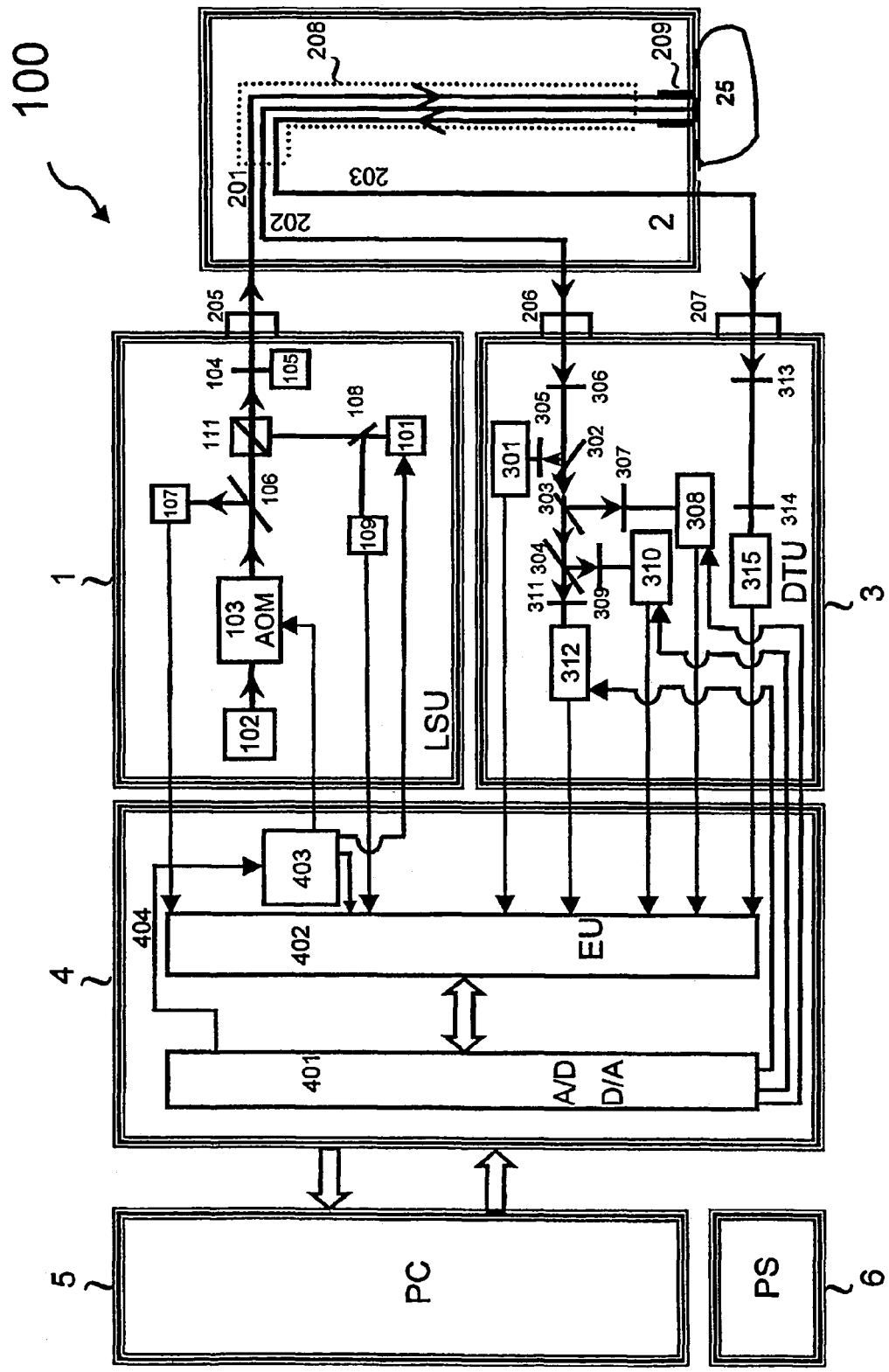
FIG. 5 illustrates schematically the main components of the first embodiment of the first aspect of the present invention.

Referring in particular to FIG. 5, in the preferred embodiment of the present invention the first radiation source (22) is a laser light source (102) for laser Doppler Flowmetry (LDF), and the second radiation source (24) is a monochromatic light source (101) of specified wavelength for monitoring at least one of NADH, blood volume and oxy-deoxy haemoglobin levels. Both light sources (101), (102) are comprised in a light source unit (LSU), shown at (1).

The probe (2) is preferably disposable, but may be semi-disposable or non-disposable. The term "disposable" in the present application means that the probes are designed (in corresponding embodiments) to be disconnected from the rest of the apparatus (100) and thrown away or otherwise disposed off after one use with only negligible economic loss. Negligible economic loss herein means an economic loss per probe which is substantially less than that of the apparatus (100) itself, or of the medical costs associate with a procedure using said apparatus (100), or indeed of the costs associated with sterilising and reconditioning the probe for a single subsequent use. The term "semi-disposable" herein means that while the probe is disposable, it may nevertheless be used a limited number of times, with appropriate sterilising and reconditioning thereof between uses. The term "non-disposable" herein means that the probe (2) is designed for multiple use, and is only disposed of when sterilisation and reconditioning thereof is no longer possible or economic. Thus, the probe (2) is typically designed for once-only use for minimising risk of cross-infection, for example. Optionally, though, the probe (2) may be adapted for sterilisation using an ETO or any other suitable sterilization technique, enabling the probe to be semi-disposable or non-disposable. In any case, the probe (2) is also typically made from biocompatible materials.

The probe (2) is operatively connected, in addition to the LSU (1), to the following:—a detection unit—(DTU) (3), a signal processing and conditioning electronics unit—(EU) (4), a suitable computer (PC) with dedicated software (5), and a suitable power supply—(PS) (6), which are also comprised in apparatus (100).

Radiation of two wavelengths (WL1), (WL2) from the LSU (1) is delivered to the tissue (25) to be monitored via a single optical or excitation fiber (201) (or bundle thereof). The excitation fiber (201) and the collecting fibers (202) and (203) are placed in direct contact with tissue (25) in order to maximize the portion of light signal that penetrates the tissue and is subsequently collected from the tissue.

The photons of the penetrating light undergo scattering and absorption as they interact with the body tissue matter. The scattering of excitation light is mainly due to interaction with stationary tissue and with the red blood cells. The absorption of the excitation light of the second wavelength (WL2) is mainly due to tissue and blood haemoglobin, and to a lesser extent is due to NADH molecules. Some of the energy that is absorbed by NADH is re-emitted by NADH molecules as fluorescence photons, a small portion of whom eventually reaches the tissue surface, and are collected by one or more collection fibers (202) and transmitted to the DTU (3). Doppler shift changes in the radiation of first wavelength (WL1) give a measure of the blood flow rate, and such changes are detected via one or more collection fibers (203).

The DTU (3) comprises appropriate optical filters and detectors for converting the collected light intensities to electronic signals from which the four tissue vitality parameters may be monitored. The converted signals from the DTU are fed into the EU (4) for processing.

The EU (4) serves as a conditioning and signal processing system. It also converts the analogue signals to digital data that feeds into computer (5). The acquired data is processed by suitable software and may displayed by any suitable means and form, such as for example on the computer screen as charts and in digital form. The PS unit (6) provides each of the components of the apparatus (100) with the required electrical power.

Excitation fiber (201), and collecting fibers (202) and (203), are provided with optical connectors (205), (206) and (207), respectively, to enable convenient coupling of the fibers to the LSU (1) and to the DTU (3) respectively.

The light from collecting fiber (203) is collimated by a suitable lens (313) within the DTU (3), and the collimated light passes through a long-wavelength pass filter (not shown). The said filter blocks out any reflections at the excitation wavelengths (WL2) and enables the passage of the longer wavelength reflection at excitation wavelength (WL1). The light that passes through this filter is then channeled towards a low-noise, fast photodiode detector (315). Preferably, a suitable condensing lens (314) is used in order to fill the photo-detector active area. The signal thus obtained from the photodiode detector (315) is used to perform Laser Doppler Flowmetry measurements in the usual manner, to determine the blood flow rate tissue viability parameter.

The light from collection fiber (202) is also collimated by a suitable lens (306), passing first through a cut-off filter (not shown) which enables the shorter wavelengths, including reflection at (WL2) and the NADH fluorescence to pass through, while blocking the higher wavelengths such as reflection at wavelength (WL1). The resulting collimated and filtered light beam is then split by a series of dichroic mirrors or beam splitters (302), (303), (304).

The light collected by the collection fibers (202) consists mainly of reflected light at the excitation wavelength, but it also comprises much lower intensity NADH fluorescence light at higher wavelengths. The portion of the collimated beam comprising the reflected light will thus have the lowest wavelength, corresponding to the excitation wavelength, while at the same time having the highest intensity of the radiation collected by the collecting fiber (202). Thus, the first dichroic mirror (302) splits off light at the excitation light wavelength from the collimated beam., channeling this portion of the beam towards a low-noise, fast photodiode detector (301). Preferably, a condensing lens (305) is used in order to fill the photo-detector active area. The dichroic beam splitter (302), therefore reflects most of the light at excitation wavelength and while permitting transmission therethrough for most of the higher wavelengths in the collimated beam, and thus provides enough filtration for the photodiode detector (301), with no additional filtration being generally needed. The signal from the photodiode detector (301) is used to perform reflection measurements to determine the blood volume tissue viability parameter. The remainder of the collimated light beam continues towards the second dichroic mirror (303).

Light of wavelengths higher than the excitation wavelength passes through the dichroic mirror or beam splitter (302) and is incident on a second dichroic beam-splitter (303), which is selected to reflect wavelengths lower then about 440 nm and to transmit all higher wavelengths. The reflected light beam is passed through a suitable filter (307), preferably a 435 nm (10DF) filter, and is then fed into a first photo-multiplying tube (PMT) (308). The light transmitted through the second dichroic beam-splitter (303) is subjected to additional splitting by a third dichroic beam-splitter (304) that reflects wavelengths lower then 460 nm, but is transparent to higher wavelengths. The reflected light from the third dichroic beam splitter (304) is filtered by a suitable filter (309), preferably a 455 nm (10DF) filter, and is then incident on a second photo-multiplying tube (PMT) (310). This wavelength is close to an oxy-deoxy isosbestic point, so the fluorescence intensity as measured by this PMT (310) correlates directly with the NADH fluorescence. The light that passes through the third dichroic beam-splitter (304) is subsequently filtered by a suitable filter (311), preferably a 475 nm interference filter (DF10), and the filtered light is incident on a third photo-multiplying tube (PMT) (312). The precision of all above-mentioned filters are ±5 nm.

The fluorescence intensity measurements provided by the first, second and third PMTs (308), (310) and (312) respectively, are used to determine the blood oxygenation state, i.e., the ratio of oxygenated blood to deoxygenated blood, within the tissue element, according to the second aspect of the present invention.

According to a second aspect of the present invention, a fluorescence-based method is used for determining the blood oxygenation state of a tissue element. The method may be incorporated in a dedicated probe-like device, for example, or with the other monitoring apparatuses known in the art, but particularly with the apparatus (100) according to the first aspect of the present invention. According to the second aspect of the invention, the tissue element is illuminated by an illumination radiation, and the wavelength of said illumination radiation being is preferably, but not necessarily, chosen to correspond to a suitable isosbestic point, and such that fluorescence is emitted from the tissue element. The intensity of the fluorescence emitted, as a function of wavelength, will vary according to the blood oxygenation state of the tissue element.

According to the second aspect of the present invention, the NADH fluorescence intensities at two points on either side of the fluorescence isosbestic wavelength of about 455 nm are each normalised with respect to the fluorescent intensity at this isosbestic point. Alternatively, the Fp fluorescence intensities at two points on either side of the fluorescence isosbestic wavelength of about 530 nm are each normalised with respect to the fluorescent intensity at this isosbestic point. In either the NADH or Fp case, at the corresponding said isosbestic point, the absorption by the blood does not change as the blood changes its oxygenation state. Similarly, the whole fluorescence spectra may be normalised with respect to the intensity at this isosbestic point, and such normalisation of the fluorescent intensities provides a better representation of the fluorescence spectra, as it is independent of the actual fluorescent intensities and actually compensates for any changes in corresponding NADH or Fp concentration or instrumentation factors such as fiber to tissue coupling, for example. Since the normalisation renders the absolute fluorescent intensity unimportant in itself in the oxygenation state determination, it is also possible to provide the illumination radiation at a wavelength which is not at an isosbestic point of the absorption spectrum of the oxy-deoxy haemoglobin Indeed if the excitation wavelength is not the isosbestic one, this will cause some changes in the fluorescence intensity, since these changes are only in total intensity but not in the functional form of the fluorescence spectrum as function of wavelength. Such changes disappear in the corresponding normalized spectrum. For example, excitation at non-isosbestic wavelength at about 355 nm by means of a $3^{rd}$ harmonic Nd-Yag laser, will generally result in changes in the fluorescence intensity due to oxygenation changes at excitation wavelength, additionally to the changes of the form of the emission curve. Referring to the NADH case by way of example, by normalizing the fluorescence emission spectrum by the fluorescence intensity at the isosbestic wavelength of about 450 nm, changes due to oxygenation changes at the excitation are effectively cancelled out.

Figure 6A:
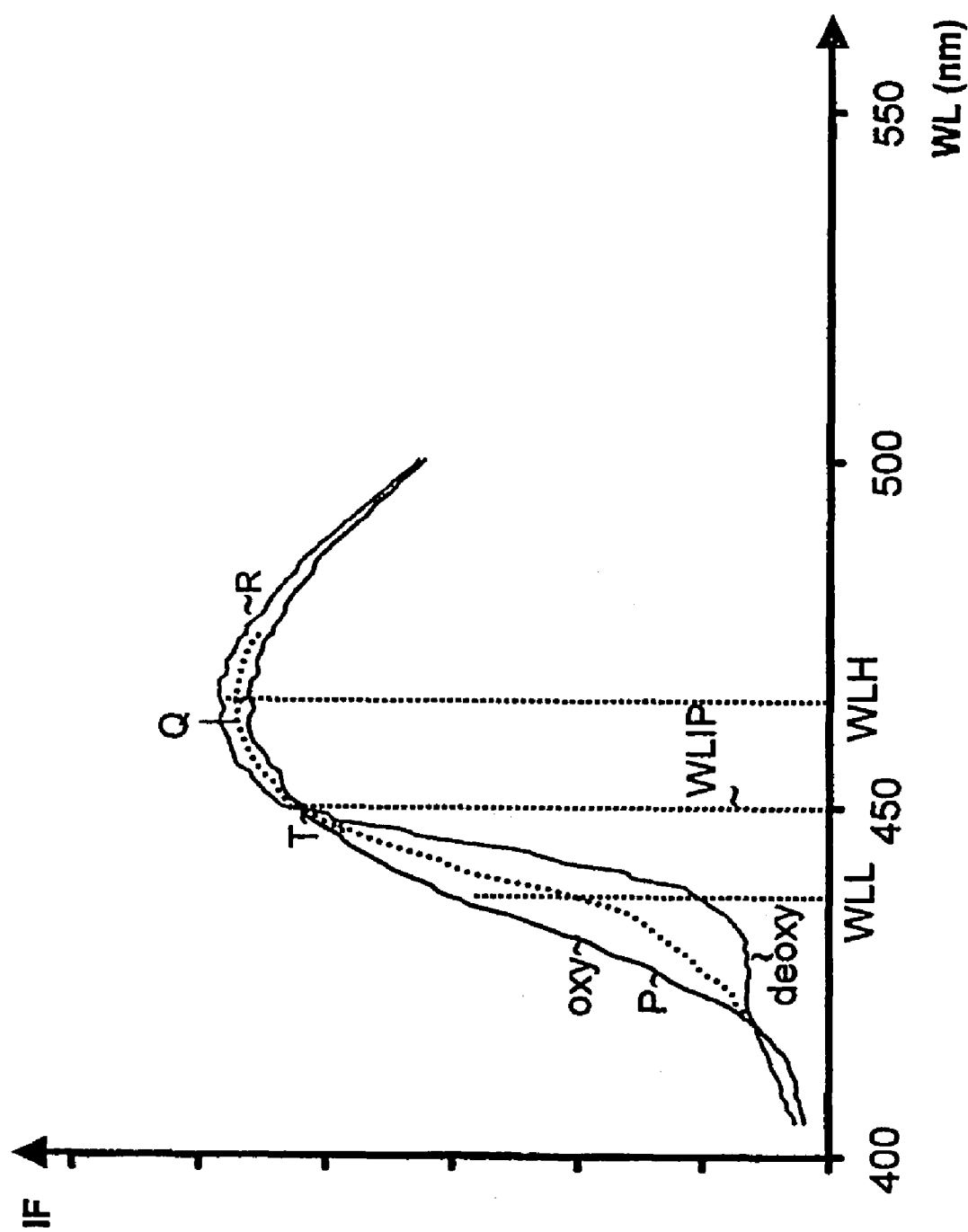
FIG. 6($a$) illustrates schematically the normalised fluorescence intensity (IF) emitted by a tissue as a function of wavelength (WL) and oxygenation level of the blood contained in the tissue.

Thus, referring to FIG. 6(a), curve (P) represents the intensity of the NADH fluorescence (IF), emitted for the full range of wavelengths (WL) of the emission when the blood in the tissue element is fully oxygenated, while curve (R) shows the corresponding (IF)-(WL) relationship for the fully deoxygenated condition. Curve (Q) represents an intermediate condition in which the blood is partially oxygenated and partially deoxygenated. All the curves pass through point (T), which is herein referred to as an "oxy-deoxy" fluorescence emission isosbestic point, corresponding to a wavelength of (WLIP). This oxy-deoxy emission isosbestic point will be at the same wavelength as the isosbestic point of oxy-deoxy haemoglobin absorption spectrum namely 455 nm as shown in FIG. 10. The actual absolute values of the fluorescence intensities will depend on the illuminating radiation wavelength, but this dependence disappears by normalising the emission spectrum by the value of fluorescence intensity at the oxy-deoxy emission isosbestic wavelength (WLIP) of about 455 nm as shown in FIG. 6(a). Thus, normalised fluorescence emission spectra obtained at a plurality of illuminating radiation wavelengths will go through a common normalised point (T), regardless of the illuminating radiation wavelength.

By measuring the ratio of the intensity of the fluorescence at a wavelength below (WLIP), say at (WLL) to the fluorescence intensity at (WLIP) and also at a higher wavelength, the ratio of the intensity at say (WLH) to the intensity at (WLIP), the actual blood oxygenation state can be determined.

Figure 6B:
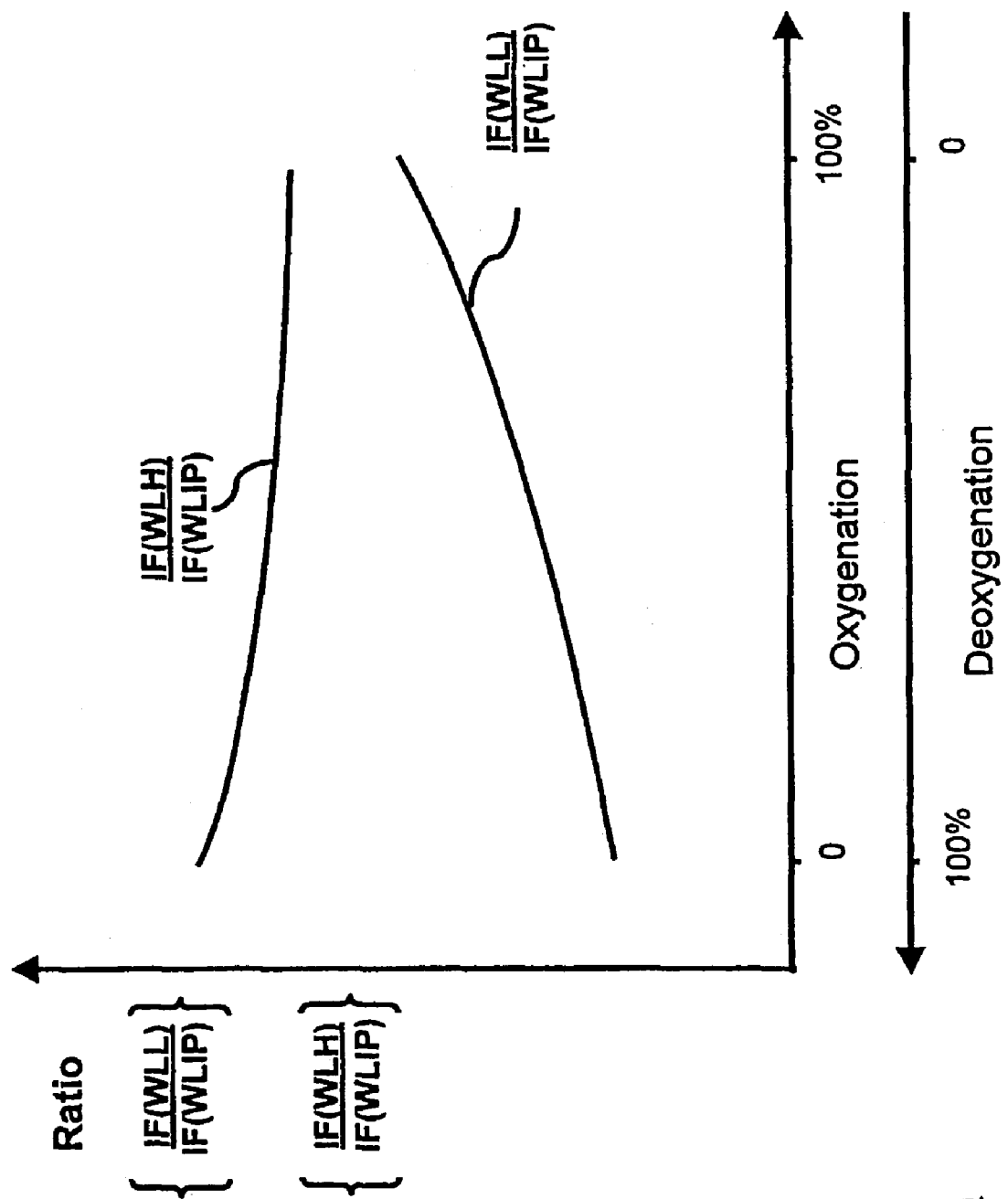

Thus, and referring to FIG. 6(b), if the normalised fluorescence intensity, i.e., ratio IF(WLL)/IF(WLIP) is increased, then the blood is substantially mostly oxygenated, while the converse is true if the intensity ratio decreases. An increase in the normalised fluorescence intensity, ratio IF(WLH)/IF(WLIP), indicates that the blood has become more deoxidized. By suitable calibration, particularly of the maximum and minimum normalised intensities (IF) at these wavelengths, the actual relative percentages of oxygenated to deoxygenated blood may be determined given the fluorescence intensities measured at these points. In order to maximize the sensitivity and precision of the method the (WLL) and (WLH) should be chosen in such a way that the change of the ratio IF(WLL)/IF(WLIP) and IF(WLH)/IF(WLIP) will be maximised with respect to oxy-deoxy relative concentration variations.

Therefore, the wavelengths where this change is maximal, $(WLL)_{MAX}$ and $(WLH)_{MAX}$, should be used. Indeed, greater sensitivity to even minor changes in blood oxygenation may be achieved by monitoring the ratio of the aforementioned ratios IF(WLL)/IF(WLIP): IF(WLH)/IF(WLIP) which is, of course, equivalent to the ratio of IF(WLL)/IF(WLH).

The electronic and electro-optic components described herein are given by way of example. There are many alternative methods of realizing the current invention. For example, although the monitoring of the three parameters is accomplished with PMT detectors, optical filters and dichroic splitters in the embodiment described herein, it is possible to replace all these components by using a grating spectrometer and appropriate detector such as a CCD or by using a multianode PMT with a Multi-band interference filter such as Hamamatsu R5900F-L16. These solutions could potentially monitor intensity ratios with even higher precision, but at current prices, are not economical options.

Thus, the present invention is also directed, in the second aspect thereof, to a suitable apparatus for determining the blood oxygenation level of a tissue element, the apparatus comprising an illumination means capable of illuminating the tissue element with radiation at a particular wavelength, preferably but not necessarily corresponding to a suitable isosbestic point of the absorption spectra for oxyhaemoglobin and deoxyhaemoglobin, and detection means for detecting the intensity of the fluorescence emitted by the tissue, at least at two wavelengths. These two wavelengths are any two different wavelengths chosen from the oxy-deoxy isosbestic wavelength (WLIP), a wavelength (WLH) higher than (WLIP), and a wavelength (WLL) lower than (WLIP). Preferably, the detection means detect the intensity of the fluorescence emitted by the tissue, at all three wavelengths. Preferably, the wavelengths (WLL) and (WLH) must be chosen to be at the point where maximal change in fluorescence intensity occur and at two different sides of the isosbestic point (WLIP). Typically, the fluorescence emission spectrum is normalised by the fluorescence intensity at the oxy-deoxy fluorescence isosbestic wavelength (WLIP), which for NADH is about 455 nm±5 nm.

Similarly, the method and apparatus according to the second aspect of the present invention adapted with respect to the Fp fluorescence is similar to that described herein with respect to that adapted with respect to NADH fluorescence, mutatis mutandis, with the main difference that normilisation of the fluorescence intensities is with respect to the fluorescence intensity at a corresponding Fp oxy-deoxy fluorescence emission isosbestic wavelength, typically about 530 nm±5 nm.

Returning now to the first embodiment according to the first aspect of the present invention, blood oxygenation level is provided by the first, second and third PMTs, (308), (310) and (312) respectively, in accordance with the second aspect of the present invention, and wherein the second PMT (310), in which fluorescence intensity is measured at an isosbestic point, also provides the NADH parameter. Thus, the ratio of the fluorescence intensity measured by the first PMT (308) to the intensity measured by second PMT (310), generally increases as the blood becomes more oxygenated, while the ratio of the fluorescence intensity as measured by the third PMT (312) to the intensity measured by the second PMT (310) under the same conditions will decrease. Conversely, as the blood becomes more de-oxygenated, the fluorescence intensity ratios measured by the first PMT (308) and by the third PMT (312) relatively to the intensity measured by second PMT (310) generally will decrease and increase, respectively. The measured fluorescence ratios can be calibrated to actual levels of oxy-deoxy haemoglobin using measurements by other known methods, such as pals-oximetery. Thus relative levels of oxygenated blood to deoxygenated blood within the tissue element may be determined.

By way of example, a suitable component for the PMT detector modules (308), (310) and (312) is the Hamamatsu 6780 PMT. Each of the PMT detector modules (308), (310), and (312) comprise a PMT tube and all electronics necessary for the PMT gain control. These modules are supplied with the operation voltage and each module has gain control input and signal output connections. The electronics circuit for all 3 PMT detectors is identical so only PMT detector (312) will be described.

The signal output of the PMT detector (312) is fed to the conditioner (402) input. There are several ways of accomplishing the signals processing which are well known in the art. All detectors in the proposed system are synchronous detectors. The appropriate electronic circuit is described below.

Thus, in the first embodiment, the same fiber (201) is used for illumination by both the first wavelength (WL1), typically a laser incident light wavelength, and the second wavelength (WL2), typically a UV monochromatic wavelength. Two sets of detection fibers (202) and (203) are situated at specific distances, R2 and R1, from the illumination fiber (201) to ensure that the tissue monitored by both the UV monochromatic and the laser incident light wavelengths is from the same layer (D1) of tissue (25).

In the first embodiment, particularly when used for monitoring brain tissue, the second light source (101) provides monochromatic UV light with wavelength of about 390±5 nm for monitoring the NADH, blood volume and oxy-deoxy haemoglobin level (blood oxygenation state). This light source (101) may be a filtered spectral lamp such as mercury or xenon lamp, a light emitting diode—LED, or a suitable laser such as laser diode. The specified wavelength for (WL2) thus complies with the two important properties hereinbefore discussed:—it falls in the absorption spectrum of the NADH molecule, and it is at an isosbestic point of the haemoglobin oxy-deoxy absorption spectrum. It is thus a preferred wavelength for both NADH fluorescence excitation and for blood volume measurements by reflection. The first light source (102) may be provided by any suitable laser of suitable intensity, coherence length and optical noise, having a wavelength greater than about 440 nm.

As hereinbefore described, the first embodiment of the present invention employs two separate radiations at different wavelengths for illuminating the tissue element, and thus the blood flow rate measurement may be conducted totally independently from the monitoring of the other tissue viability parameters, albeit within the same tissue layer (and preferably the same tissue volume) providing a great deal of flexibility in terms of configuration of the monitoring apparatus, as well as in the method of use.

In general, it is preferable that all four parameters, namely the first set for measuring blood flow, and the second set, for measuring NADH, blood volume and blood oxygenation level, are monitored with irradiation and detection occurring with high sampling frequency, however this may give rise to safety issues regarding the excitation radiation used for the measurements. In particular, the monitoring of the second set of tissue viability parameters—NADH fluorescence, blood volume and blood oxygenation level, requires use of excitation wavelengths between 300 nm and 400 nm, which lie in the UVA spectral region; the exposure to which should be minimised as it is considered to be potentially dangerous even at low irradiation levels. The monitoring of the first parameter namely the blood flow by laser Doppler technique also raises safety issues, especially where the laser Doppler utilizes irradiation inside UVA region, since a higher irradiation intensity, is required for Doppler measurements than that needed for the measurements of the second set of parameters, and even when the laser Doppler wavelength is in the visible spectral region, there are still safety concerns due to the relatively high irradiation intensity required. In order to minimise the problem, the option is provided in the present invention to chop the excitation light with a duty cycle of 1/20 (ON/OFF). Additionally there are many clinical conditions where continuous monitoring with frequent updating is unnecessary, and this constraint may therefore be relaxed. Thus, whereas during critical parts of a surgical operation procedure the output data should be renewed at least at the rate of two data points per second, there are however, many cases where the patient's condition is stable, so that a data sampling rate of only, say, once every two seconds is required, for example.

According to the present invention the apparatus (100) may be used according to an adaptive chopping procedure. In such an adaptive chopping procedure, the radiation provided by each one of sources (101) and/or (102) may be chopped to provide corresponding pulses of radiation at the appropriate wavelengths, the pulses being provided at a preferably variable frequency of pulsation, i.e., chopping frequency. Furthermore, the apparatus (100) may be further adapted such that packages of pulses may be provided as and when required or desired. Such packages may each comprise a variable number of pulses, and the time interval between packages of pulses may also be independently controlled. Thus, at periods where relatively little monitoring is required, few packages containing a few pulses each may be transmitted with large "OFF" intervals in-between packages (i.e., where no radiation is provided), while at other, more intense periods, the packages of pulses may be sent with little or no intervals between successive packages. By pulsing, and by also packaging the pulses as described, the radiations provided by sources (101) and also by (102) may be of a correspondingly higher permitted intensity than would normally be allowable, albeit for shorter durations. This results in better signal-to-noise ratios of the signal, as well as to safer radiation levels for both the patient and the operators of the apparatus and equipment.

Using the concept of adaptive chopping, it is possible to entirely stop the laser Doppler measurements after this parameter has reached a steady state. The remaining three parameters, the second group, may be measured by providing short packages of pulses at a frequency of, say, twice a second. Indeed the second set parameters will also be in steady state until some change occurs. If the change originates in the blood flow rate, it will immediately induce a change in the other, actively monitored parameters, such as the blood volume. The apparatus (100) may then be configured such that when such a change is detected, the Laser Doppler measurements automatically restart and continue until at least the next steady-state condition is reached.

Thus, referring to FIG. 5 and also FIG. 7(a), the laser radiation or light from source (102), typically a stabilized laser diode, is chopped by an Acousto-Optic Modulator (AOM) (103). A clock (403) that is part of the EU (4) generates the chopping sequence. The chopped light appears at the $1^{st}$ order of the modulator. This order is spatially filtered by a circular diaphragm (not shown) and coupled to an excitation fiber by the lens (104) mounted on a suitable adapter (105). The excitation light is split by a beam splitter (106) and a small portion of it is directed towards a photodiode (107). This photodiode provides tracking of the excitation intensity of light source (102).

A similar beam-splitter (108) may also be utilized with the other light source (101), typically monochromatic 390±5 nm light source, and a small portion of signal is directed towards photodiode (109). This photodiode provides tracking of the excitation intensity of light source (101).

The radiations originating from the two light sources (102) and (101) are combined to be colinear by the cube beam combiner (111). Preferably, the polarisations of the two radiations are mutually perpendicular, providing advantages in their transmission efficiencies.

The outputs of the photodiode detectors (301), (315), (107) and (109) and the outputs of the three PMT detectors (308), (310), (312) are connected to the signal conditioner (402). The signal conditioner (402) receives synchronization signals that correspond to the chopping sequence from the clock (403). The signal conditioner features three groups of 'channels' or synchronous detector circuits, which will be described below.

The signal conditioner (402) of the EU (4) converts the chopped signals into continuous wave (CW) signals. These are converted by the A/D unit (401) into digital data, which is then fed into the computer (5) through the analog input output (AIO) ports. The A/D sub-unit (401), besides digitizing the analog measured signals, also enables the receiving of digital commands from the computer (5) via the digital input output (DIO) ports.

The clock (403) sub-unit provides the appropriate timing for the AOM (103) and the signal conditioner (402).

In the first embodiment, the source (102). may consist of a single mode laser having a wavelength of 532 nm for laser Doppler Flowmetry measurements, while the source (101) may provide, for example, a 325 nm, 337 nm or 390 nm monochromatic excitation wavelength used for NADH fluorescence, the resulting 415–470 nm emission wavelengths being used for NADH fluorescence and blood oxygenation measurements. Such an arrangement is suitable for brain gray matter, wherein the penetration depth (PD) for a 532 nm wavelength is 0.6 mm while for 325 nm or 337 nm or 390 nm wavelengths, the PD is only 0.2 mm, as illustrated in FIG. 2. Since the ratio of the PD of these two wavelength groups is 3, in order to maintain the same average sample depth (SD) for both groups of tissue viability parameters, there should be a 1/3 ratio for the distance between the excitation to the collection fibers of the two groups, i.e. for R2/R1.

While the first embodiment is used preferably with the source (102) providing a radiation of wavelength substantially higher than 440 nm, it may also be used with a source (102) providing radiation of wavelength between 300 nm and 440 nm. Since the wavelength of the other source (101) is also within this band, the ratio R1:R2 is close to unity, since the penetration depths for such a range of wavelengths is about constant (see FIG. 2). Thus, rather than having two separate collection fibers (202) and (203), the functions of these fibers may be accomplished by single fiber, or indeed a plurality of such single fibers, each of which may have the combined functions of fiber (202) and (203). (Of course, separate fibers (202), (203), or pluralities thereof, may also be used.)

Figure 4B:
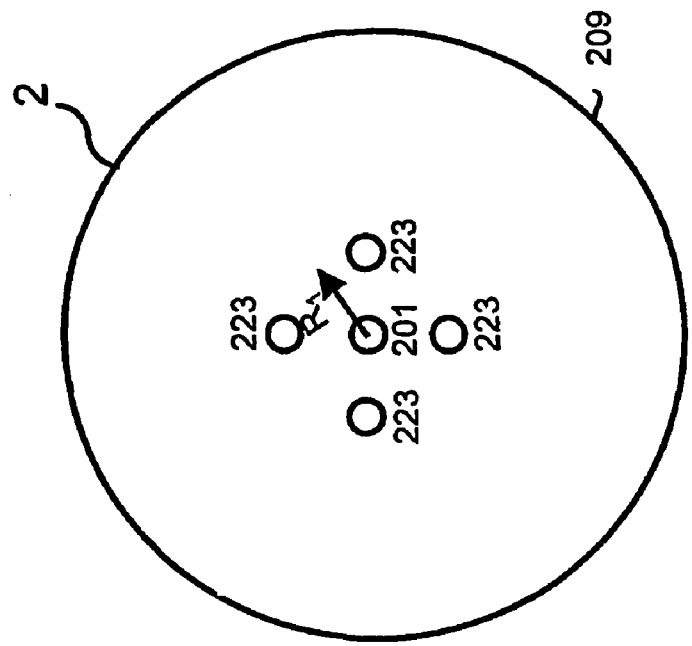
FIG. 4($a$) illustrates in end view the embodiment of FIGS. 3($a$) and 3($b$) taken along X—X.
Figure 4A:
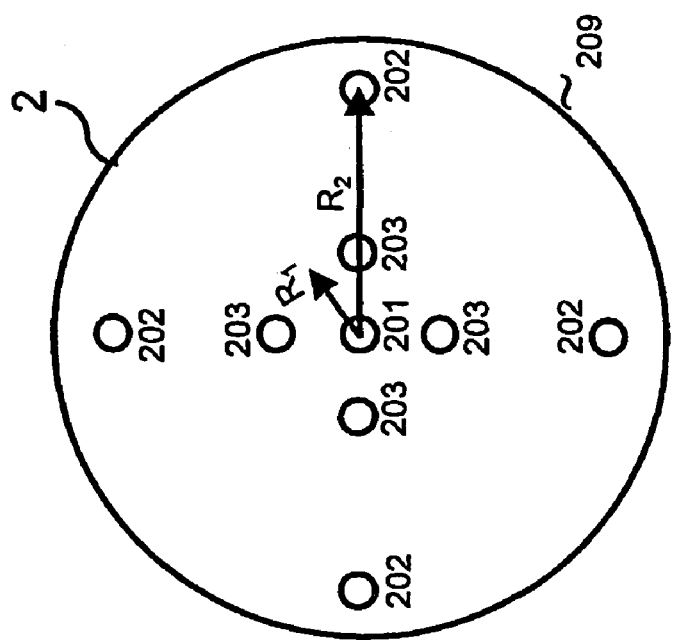
Figure 8:
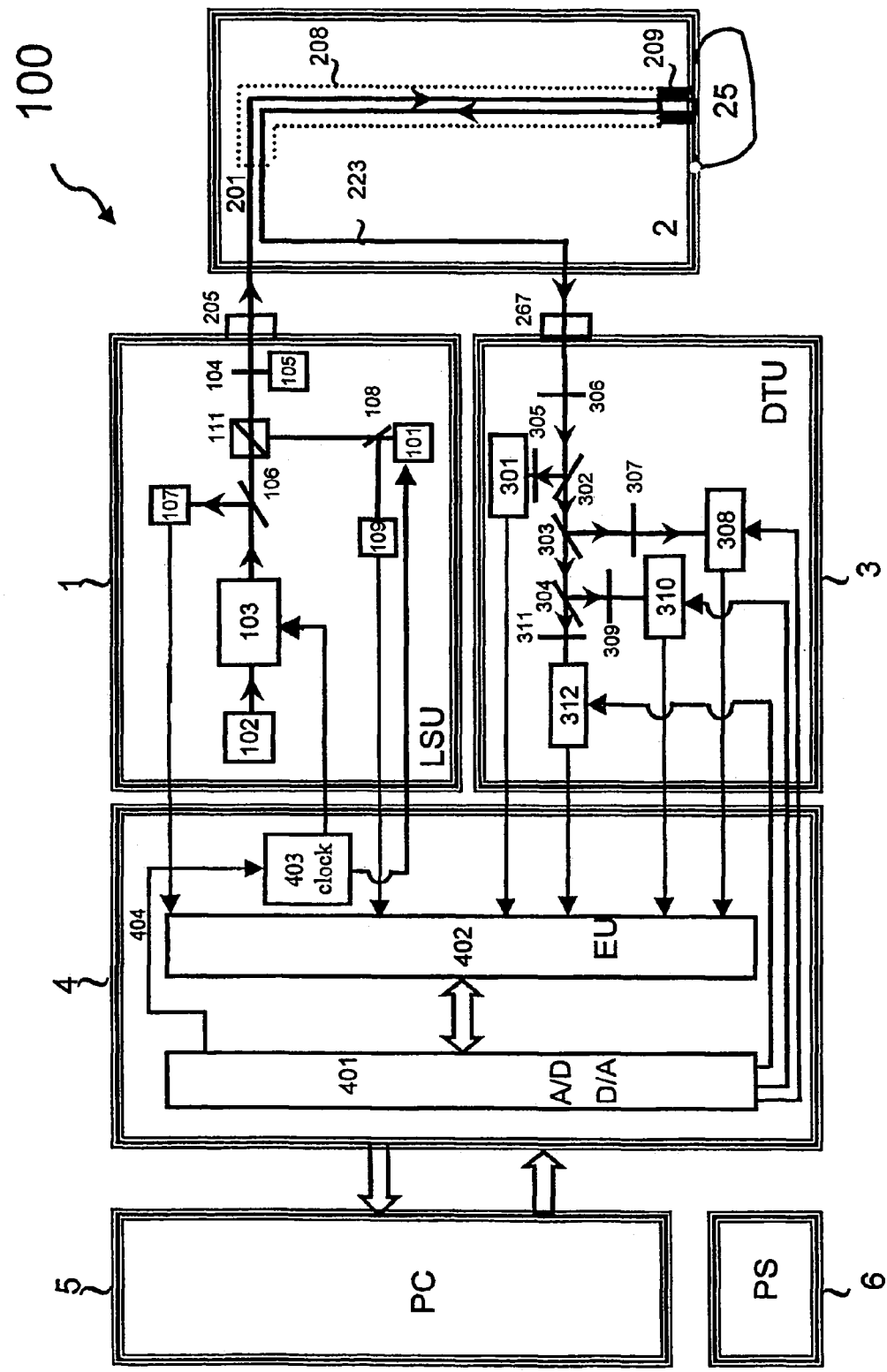
FIG. 8 illustrates schematically the main components of the second embodiment according to the first aspect of the present invention.

Thus, a second embodiment of the present invention, illustrated in FIG. 8 and FIG. 4(b), comprises the same structural elements as the first embodiment, with the exception of the said collection fibers (202), (203) (including said optical connectors (206), (207), and lens (313), condensing lens (314) and fast photodiode detector (315)), as hereinbefore described, mutatis mutandis.

In the second embodiment of the invention, the choice of laser light for source (102) as used for LDF monitoring is limited to the 300–440 nm range. Across this wavelength band, the penetration depth is almost constant as taught by Eggert (Eggert, H. R. & Blazek, V., Neurosurgery, 21, 459–464, 1987), and as shown in FIG. 2. In this case, all measurements are made simultaneously with the same excitation and the same collection fibers, and virtually the same volume element of tissue is monitored for the 4 parameters—blood flow rate, and the three parameters of the second group, i.e., NADH, blood volume and blood oxygenation state. Many other tissues also display similar penetration depth plateaus at various wavelength ranges, and one should appreciate that suitable embodiments could be devised for applying this inventive concept for monitoring blood parameters for such tissues, mutatis mutandis. In this second embodiment, a light source (101) such as, for example, filtered spectral lamp, light emitting diode LED, laser diode or pulsed laser, is used for excitation of NADH fluorescence. The light source wavelength can be any wavelength that is inside the absorption spectrum of the NADH molecule, that is having a wavelength of from about 315 to about 395 nm. To avoid the Haemodynamic artifact, and to enable measurement of oxy-deoxy haemoglobin, this wavelength is preferred to be at one of the haemoglobin oxy-deoxy isosbestic points in this bandwidth. There is no requirement for laser Doppler measurements to be performed at one of these isosbestic wavelengths.

Referring to FIGS. 8 and 4(b), only one (or a plurality of) collection fiber (223) and connector (267) are required instead of the individual collection fibers (202), (203) (or corresponding pluralities thereof), and the connectors (206), (207) that are required for the first embodiment. The signal from photodiode detector (301) is then used for LDF blood flow rate monitoring as well as the reflection measurements for blood volume parameter.

As in the first embodiment, the light from the collecting fiber (223) enters the DTU (3) via optical connector (267). The collimating lens (306) collimates the light towards the first dichroic mirror (302), which splits off the excitation light wavelength, which is then channeled towards a low-noise, fast photodiode detector (301), a condensing lens (305) being typically used in order to fill the photo-detector active area. The signal from the photodiode detector is used to perform both Doppler and Reflection measurements.

Thus the reflection at both detection wavelengths (W1) and (WL2) will, in this embodiment, pass through the same collecting fiber (223). The separation of these different signals is achieved by time-sharing. The light sources (102) and (101) are working in chopping mode therefore each source is ON only for a short time period as is described hereinafter. Each light source has a low duty cycle, therefore there is plenty of time to turn ON one light source while the other one in still in the OFF period. Each one of the corresponding detectors (107) and (109) is synchronously sampled at the correct timing in order to get intensity information regarding the corresponding excitation source. The detector (301) is sampled twice, once for the measurement of reflection at WL1 and corresponding laser Doppler measurements and a second time, for reflection measurement at WL2. Both reflections at WL1 and WL2 have substantially lower wavelengths than the NADH fluorescence and therefore the same dichroic beam splitter (302) can be used for separating these two relatively strong reflections from the weaker fluorescence signal.

In embodiments where the Doppler excitation wavelength WL1 lies in the range 420 nm to 440 nm, in either the first or second embodiment, the resulting NADH fluorescence will not pass through the dichroic beam splitter (302) designed to split these wavelengths towards detector (301). To overcome this problem at these wavelengths, a simple 1:20 beam-splitter should be substituted for the fore-mentioned dichroic beam splitter. It should be noted, that the strong WL1 reflection will not interfere with the NADH fluorescence, despite the two signals having similar wavelengths, because the signal are separated in time.

While the appropriate illumination wavelengths for sources (101), (102) referred to hereinbefore are particularly suited for the monitoring of brain tissue in-vivo using the first and second embodiments, corresponding illumination wavelengths may be determined for any other tissue enabling the apparatus (100) to be used with such tissues, mutatis mutandis.

In order to reduce the tissue irradiation the apparatus (100) according to the present invention may be operated in any one of several irradiation modes, and corresponding to these modes are several data acquisition modes. There are two basic concepts behind these operation modes:

The first concept relates to monitoring that is perceived to be continuous by the clinical personnel. In general, all vitality signals data should be presented to the medical personnel in real-time. That is, the device display should be updated at the rate that reflects the real physiology events as they evolve in the patient. This means that if for example the patient is in a critical stage of the surgery and there are a lot of fast changes in the physiological conditions, the screen update rate should be fast i.e. about two data points per second. However, where the patient is in a more stable condition such as at the beginning of the surgery, at its final stage or in the intensive care unit (ICU), the vital parameters will generally tend not to change very fast, and therefore a much slower screen update rate can be utilized. In such cases the update rate can be for example one data point every 2 seconds.

The second concept is that actually all vital parameters are mutually connected and inter-related. Therefore a change in one parameter should immediately trigger a change in at least one other parameter. Especially any change in the blood flow will be accompanied by a change in at least one of the other parameters: blood volume, blood oxygenation or the NADH fluorescence. This means that if the patient's state is steady, such as in ICU, the monitoring of the blood flow can be stopped for long periods whilst all the other tissue vitality parameters are monitored. Where any significant change in the value of any one of these parameters is detected the system will automatically start monitoring of all parameters including the blood flow, until a steady state is again reached.

Figure 9A:
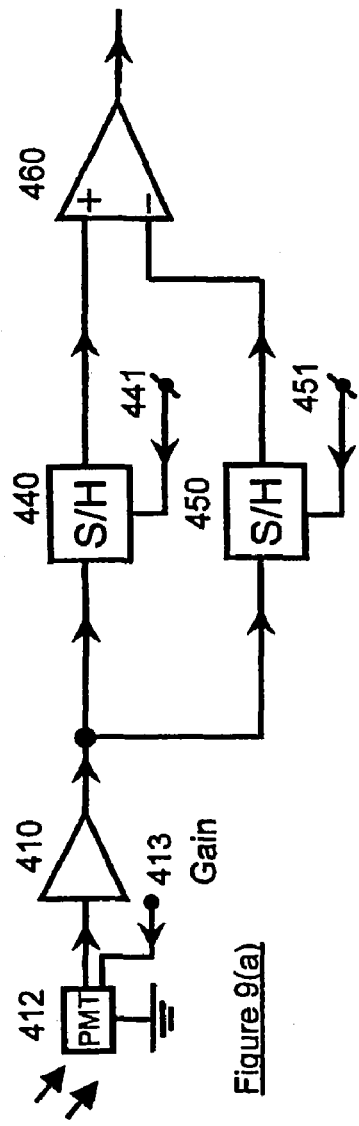
FIG. 9(a) schematically illustrates a circuit diagrams for a signal detector optionally used with the embodiments of FIG. 5 and FIG. 8.
Figure 9B:
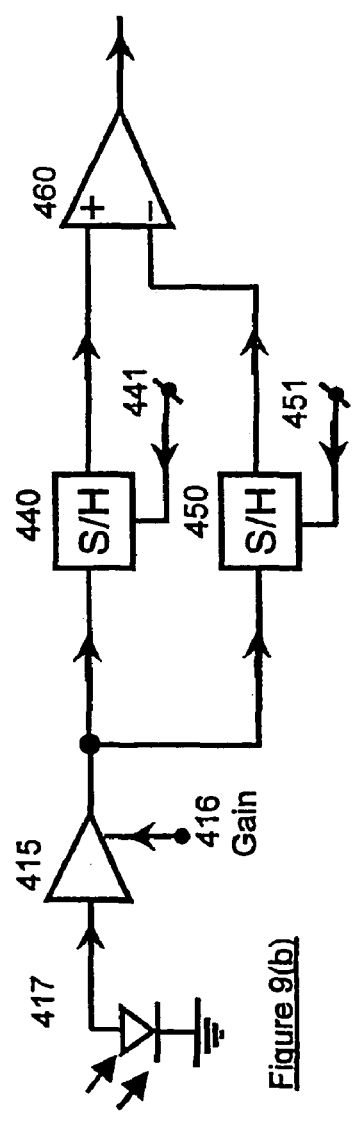
FIG. 9(b) schematically illustrates a circuit diagrams for another signal detector optionally used with the embodiments of FIG. 5 and FIG. 8.
Figure 9C:
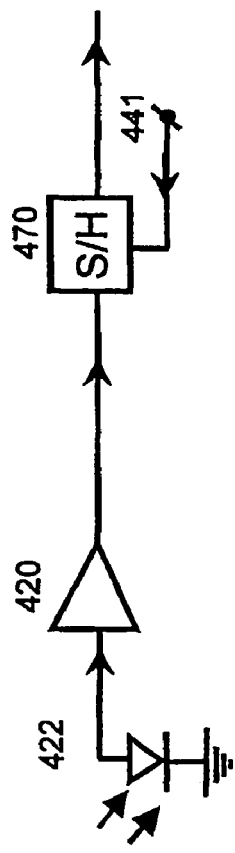
FIG. 9(c) schematically illustrates a circuit diagrams for another signal detector optionally used with the embodiments of FIG. 5 and FIG. 8.

Referring now to FIGS. 9(*a*), 9(*b*) and 9(*c*), In a specific, non-limiting example of the preferred embodiments brought for illustrative purposes, three types of optical detectors with corresponding electronics circuits are used.

The first type of detector as shown in FIG. 9(*a*), is a photon multiplier tube (PMT) detector. This type is suitable for use as components (308), (310), (312) shown in FIGS. 5 and 8. These detectors are used for NADH fluorescence measurements. The detector is build around a PMT module from Hamamatsu H6780. This integrated module consists of PMT tube, a high voltage power supply and all necessary control electronics. One need only to supply the operating voltage and the control voltage for the gain control, and the module itself changes the high voltage of the PMT accordingly. The gain of such detector may be controlled by the PC (5) through the A/D (401) unit. The output of this PMT module is fed to the inverter (410), since the module produces negative output relative to ground. The output of the inverter is feed to dual sample and hold (S/H) circuits built around S/H such as Analog Devices AD781 (440) and (450). The dual S/H circuit enables subtraction of the dark current and background light that might interfere with the desired measurements.

The second type of detector, illustrated schematically in FIG. 9(*b*), is a fast photodiode detector such as (301) and (315) (see FIG. 5) and (301) (see FIG. 8). These kinds of detectors are used for reflection and Doppler measurements. This type of detector is build around Hamamatsu S5973 photodiode (417) connected to trans-impedance amplifier such as Analog Device AD713 (415). The output of the trans-impedance amplifier (415) is fed to dual sample and hold (S/H) circuits build around S/H such as Analog Devices AD781 (440) and (450). The dual S/H circuit enables subtraction of the ambient light that might interfere with the desired measurements. This circuit is identical to the circuit used for PMT based detector and will be described later.

The third type of detector, illustrated in FIG. 9(*c*), is a fast photodiode detector. This is suitable for use for components such as (107) and (109), which are shown in FIG. 5 and FIG. 8. These types of detectors may be used for light source intensity measurements. The light source intensity information is used at the final stage of data processing to normalize the reflection and fluorescence intensities according to the changes in the light source intensities. This type of detector is built around a Hamamatsu S5973 photodiode (422) connected to transimpedance amplifier such as Analog Devices AD713 (420). The output of the transimpedance amplifier (420) is fed to a single sample and hold (S/H) circuit build around S/H such as Analog Devices AD781 (470). Since the light to the detector is collected from an internal source there is no need for subtraction of the background light as in previous cases, therefore a single S/H circuit can be used.

The S/H circuits for the first two types of detectors as illustrated in FIGS. 9(*a*) and 9(*b*) are substantially identical. The output of the trans-impedance amplifier (415) or the inverter (410) is connected to the first sample and hold S/H circuit (440). The S/H circuit is triggered by the clock (403). Referring to FIGS. 7(*a*) to 7(*e*); the trigger signal timing 7(*c*) provided by the clock (403) is correlated with the end of the light ON period in 7(*a*) when the output voltage 7(*b*) of the detector is at a maximum, enabling the S/H circuit to sample the maximum available signal. The S/H circuit (440) holds this voltage value 7(*e*) until a new trigger signal 7(*c*) arrives from the clock. The second S/H (450) is also connected to the same signal input as S/H (440). This S/H circuit receives a delayed hold signal 7(*d*), so that the sampling occurs between the two pulses of 7(*a*). This delay results from the delay circuit that is an integrated part of the clock (403). The sampled intensity (not shown) bears information on the detector dark current and the ambient light which both interfere with the measurement. A difference amplifier (460) such as Texas Instruments TL082 subtracts the output of one S/H from the other, the output of this differential amplifier is the measured signal.

The output of the S/H (440) consist of the desired signal along with noise such as the detector dark current, shot (electronic) noise and the ambient light. The output of the S/H (450) contains all these types of noise, but not the desired signal. The outputs of S/H (440) and SH (450) are fed into a difference amplifier (460) which subtracts the two signals, the output being the net light signal. Of course, since the shot noise is substantially random, it cannot subtracted.

The third detector circuit as shown in FIG. 9(*c*), comprises a single S/H (470). The output of the trans-impedance amplifier (420) which is identical to the amplifier (415) is connected to a single sample and hold S/H circuit (470). The S/H circuit is triggered by the clock (403). The trigger signal timing FIG. 7(*c*) is correlated with the end of the light ON period in FIG. 7(*a*) when the output voltage of the detector FIG. 7(*b*) is at a maximum, so the S/H circuit samples the maximum available signal. The S/H circuit (470) holds this voltage value until a new trigger signal as shown in 7(*c*) arrives from the clock (403). This circuit is thus very similar to the two previous ones described with respect to FIGS.

9(a) and 9(b), but here there is no background light subtraction by a second S/H since the light reaches this detector from an internal source, and is thus free from external light interferences.

The gain of the detectors is defined automatically by the accompanying software in computer (5), according to the detected light intensity values. If the detected light signal is too small, the software provides an appropriate signal to increase the detector gain as described below. There is a difference in the gain management of the three types of the detectors as described above.

The gain of the first detector type, the PMT, is set by changing the control voltage (413) of the PMF module (412). This actually changes the sensitivity of the detector PMT. The gain of the inverter amplifier (410) is constant. The setting of the control voltage is performed by the software that runs on the PC (5) through the analog to digital converter (A/D) module (401) of the electronics unit (EU) (4). This A/D and D/A module can be any one of the variety of cards produced by National Instruments and other manufacturers.

The gain of the second detector type is set by changing the transimpedance amplifier (415) gain rather then by changing the sensitivity of the photodiode detector itself. The setting of the control voltage is performed by the software that is adapted to run on the PC (5) through the A/D module (401) of the electronics unit (EU) (4).

The gain of the third detector type is constant since this detector measures light source intensity having a predefined value that suits the constant dynamic range of the detector.

The gain setting procedure is initiated by the calibration command from within the device software. The calibration signal arrives from the computer (5) via digital to analog converter D/A (401). At the beginning of the calibration procedure the gain control voltage of the first and second detector type is reduced to zero, and then, the gain gradually begins to increase whilst the intensity of the output signal is monitored. With reference to the output of the detectors (308), (310), (312) in FIG. 5 and FIG. 8 and the detectors (301) and (315) in FIG. 5 and the detector (301) in FIG. 8, each detector gain is set separately. When the output voltage reaches about 2V, the gain is locked to the current value. This gain value is monitored by the software through the analog to digital converter A/D (401). From then onwards, any change in collected light intensity is monitored by the circuit and is transformed to digital information by (A/D) (401). Since the gain value, is known, the actual light intensity may be calculated and displayed on the screen by the software.

The clock sub-unit (403) typically comprises a programmable clock. According to computer input via bus (404) the clock output will be in one of the following states (with particular reference to FIG. 7(a)–7(g)):

State I: The clock signal consists of a train of pulses in FIG. 7(a). The ON period $t_{on}$ of the cycle is 10 microsec, while the whole cycle $t_{cycle}$ is 250 microsec i.e. the repetition rate is 4 KHz. Therefore the duty cycle is 0.04. This sequence shown in 7(a) is used for enabling the light source (102) by the triggering of the AOM (103), and also is used, after appropriate delays, to trigger the signal S/H circuit (440) and reference S/H (450) by sequences 7(c) and 7(d) respectively. The sequence 7(c) is correlated to the end of each pulse shown in 7(a), while the sequence 7(d) is delayed by $t_{cycle}/4$ in order to enable to pick up the external light interference. The sequence 7(c) is also used to trigger the light source sensing detector circuit S/H (470). Another second sequence identical to 7(a) with its two delayed sequences is used for enabling light source (101) and the appropriate detectors (109), (301), (308), (310) and (312) (see FIG. 5 and FIG. 8).

This second sequence is delayed,by $t_{cycle}/2$ relative to the first sequence in order to separate in time the measurements of the two said sets of parameters.

State II: State I is additionally chopped by an ON/OFF adaptive duty cycle which enables and disables the light pulses train 7(f). During the ON period $t'_{on}$ (0.1 sec) of the adaptive duty cycle, 400 pulses 7(a) of 10 microsec each are generated. The OFF period $t'_{off}$ of the adaptive duty cycle is controlled by the computer via bus (404). The OFF period can be 0.4 sec for relatively fast-changing conditions and can be prolonged to as much as 5 sec for slow changing conditions. The $t'_{off}$ is determined automatically by the software to minimize the total tissue irradiation.

State III: The clock generates a sequence of ten cycles of the state I like the pulses shown in FIG. 7(a). These ten pulses are used for enabling light source (101) alone and the appropriate detectors (109), (301), (308), (310) and (312) on FIG. 5 and FIG. 8. Therefore measurements of only the second set of parameters are enabled.

The device software controls the tissue sampling and irradiation. At measurement initialization the clock is in state I, enabling the correct setting of the gain for all detectors, and the normalization of the output signals. After a short time, if fast changes in any one or more parameters are observable the clock is switched to state II, having a short OFF period $t'_{off}$. As the changes became more moderate, the OFF period $t'_{off}$ becomes longer. After cessation of the changes as steady state is achieved, the system switches to state III in order to minimize the tissue irradiation. Detection of changes causes the system to switch back to state II.

In state III, only 10 pulses of WL2 are supplied to the tissue during $t''_{on}$ see FIG. 7(g). This enables quick measurement of the second set of parameters using only very limited irradiation. The $t''_{off}$ of the sequence is adjusted by software according to the condition of the patient, and the total measurement time needed, so, for example, during an operation, this OFF period can be a mere 0.5 sec in order to rapidly detect any changes whereas for a patient in intensive care, this OFF period may be as much as 5 sec since there are no fast changes and, since the monitoring could be over several days, the total irradiation should be strictly controlled.

The PS (6) typically comprises an on-line medical grade power supply with an insulating transformer as required by Standard IEC 601-1 for electrical medical equipment.

The PC (5) typically comprises a Pentium II or higher system running Windows 95/98/NT or higher. The dedicated Computer and Power Supply are specified to meet EMC and other requirements for medical apparatus.

The probe (2) is typically adapted for sterilisation using an ETO or any other suitable sterilization technique, and is also typically made from biocompatible materials. Optionally, the probe (2) may be designed for once-only use for minimising risk of cross-infection, for example.

The dedicated software for the PC (5) is preferably based on the National Instruments LabView platform. The Doppler module calculates the blood flow according to well-established algorithms. The Exposure Tracking module calculates the total and the mean exposure. It also decides in which of the three possible clock modes the system will operate. When stable signals are detected for all measured parameters, the system will switch to State III. In that mode the tissue receives extremely low exposure. Only the three parameters of the second set are monitored i.e. NADH fluorescence, blood oxygenation state, and blood volume via reflection. The blood flow rate is not actively monitored. If a change is detected in the value for any one of the measured parameters, this module switches the system to State II where all four parameters are actively measured. When calibration is initiated the system is switched to State I where all four parameters are measured at high sampling rate.

The system or apparatus (100) may be operated as follows: At the beginning of the measurements the user places the probe (2) on the tissue (25) and activates the system via a terminal of the computer. This automatically initiates a calibration sequence that lasts about 1 sec. During the calibration sequence the gain of the detectors are established and fixed. During calibration sequence, the clock generates pulses according to state I.

At the end of the calibration, the computer switches the clock to state II.

When switched to state II the OFF period is set to 0.4 sec so that the system measures all parameters at the rate of 2 data points per second. If after 10 readings, (i.e. 5 sec) there is no substantial change in any of the parameters, the OFF period $t'_{off}$ is gradually increased to a maximum of 5 sec. If a steady state is attained, the clock is switched to state III. In state III ten 10 usec pulses are generated according to state I. Although this low number of pulses is insufficient for laser-Doppler measurement, it is sufficient for reflection, fluorescence and oxy-deoxy measurements. The pulse packets of state III are initiated every 0.5 sec to 6 sec depending on the monitoring mode, or until a physiologically significant change, such as, say, a 2% change in the value of any of the three parameters monitored. This change being measured relative to the value of the parameters as measured in the last state II event. After leaving state III, the system switches to state II with an OFF period of 0.4 sec.

In routine clinical use the system is preferably used in states II and III, with the mean irradiation being typically less than 0.5 mW/cm².

The Adaptive Duty Cycle enables the reduction of the tissue irradiation to a value significantly below the maximum limit imposed by the various standards, whilst still producing a high signal to noise ratio.

This is illustrated by the following calculation brought by way of example:

The light intensity emitted from the distal end of probe (2) may be in the order of about 1 mW. The limiting aperture of the probe may be typically about 0.1 cm therefore the area is 0.00785 cm², so the irradiation during the ON part of the pulse is 127 mW/cm². With the first duty cycle set at 0.04, and the second duty cycle at 0.1/5=0.02, the mean irradiation will be reduced by factor 0.04*0.02=0.0008, or in other words 1250 times less than the peak value. The mean irradiation will be 127/1250=0.1 mW/cm².

If fast changes are detected, the mean irradiation might be as much as 1 mW/cm². Although this is higher, it is still well within allowed limits. Thus, with irradiation during the ON part of the pulse being 127 mW cm², the first duty cycle being 0.04, and the second duty cycle now being 0.1 sec/0.5 sec=0.2, the total irradiation is then reduced by a factor of 0.04*0.2=0.008. In other words, the mean irradiation will be 127*0.008=1 mW/cM², and this value of irradiation can be delivered for 30,000 sec, or nearly nine hours, whilst remaining within the radiation limits of the relevant standard.

Thus, tissue may be irradiated with chopped light to provide important advantages, such as improving the accuracy in the measurements for all four parameters. Chopping enables the peak illumination intensity to be increased while holding constant the average intensity of the excitation. It allows the average excitation intensity to be reduced to within safe limits with respect to photo-damage. This can be achieved without significant loss of reasonable signal to noise levels.

"Chopped light" may be produced by chopping the excitation light illumination, and this may be achieved, for example, by an Acoustic Optic Modulator (AOM), though a fast rotating chopper wheel or any other chopping device may also serve this purpose. Similarly, direct modulation of the light source current could be used to generate the chopping effect.

In the context of this specification the duty ratio (DR) of the pulsed excitation is defined as the ratio of the duration of each pulse to the total cycle time. When the duty ratio is decreased, the signal to noise ratio is increased by factor $(DR)^{-1}$ for a parameter whose measurement is limited by background noise and by factor of $(DR)^{-1/2}$ for a parameter which signal quality is limited by white noise generated in detection apparatus (Hodby J., J. Physics E: Scientific Instruments, 3, 229–233, 1970).

The ambient light interference and the dark current noise can be compensated for. This may be done by simply measuring the detector output during the OFF period and subtracting its value from the value during the ON period as described above. Since the chopping produces Amplitude Modulation (AM) of the measuring signals, all the drift fluctuations and 1/f noise are canceled.

The third and fourth embodiments of the present invention are directed to further measuring the flavoprotein parameter, in addition to the other four parameters that are measured in the first and second embodiments, respectively.

Figure 12:
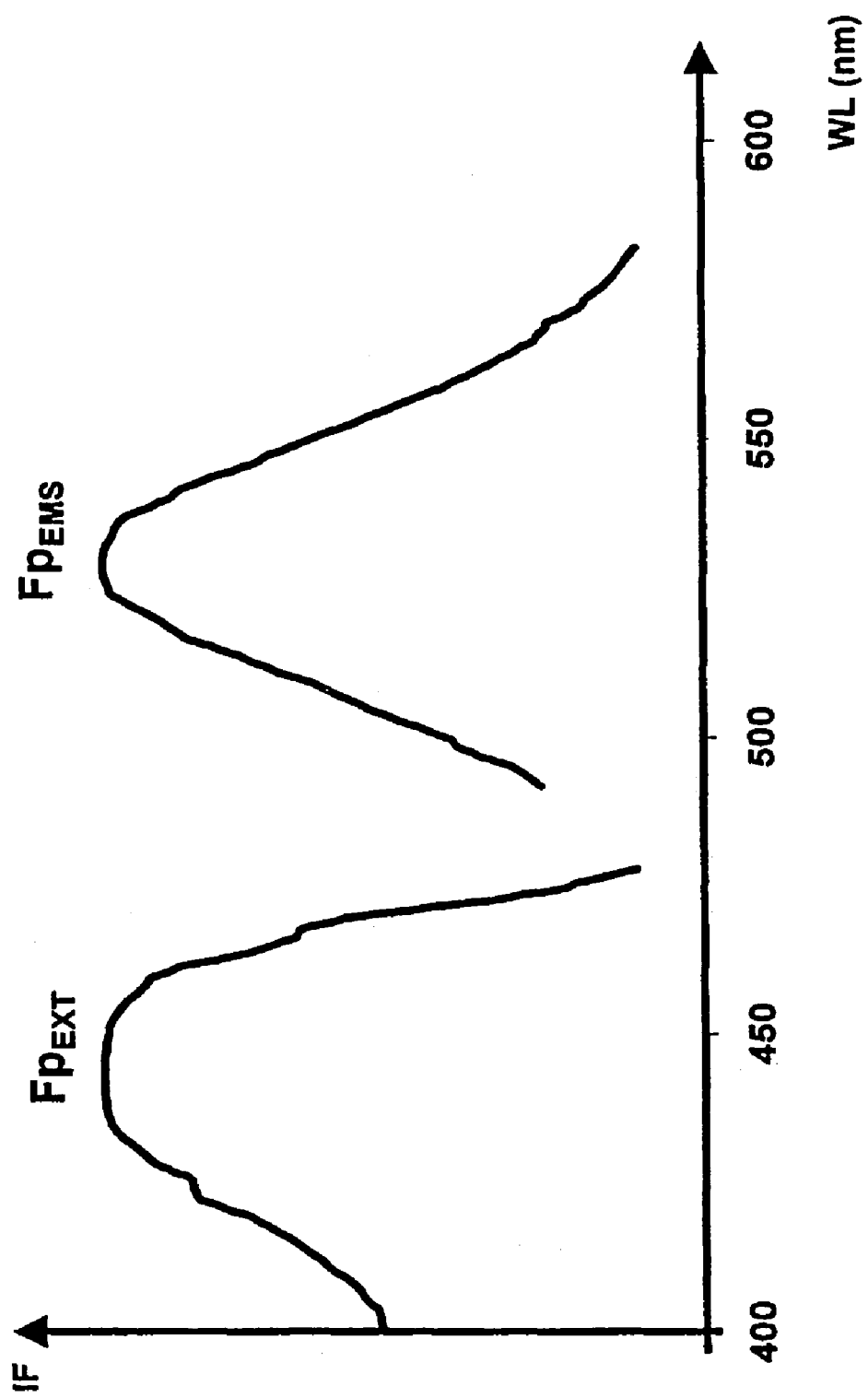
FIG. 12 shows the excitation fluorescence spectrum ($Fp_{EXT}$) and emission fluorescence spectrum ($Fp_{EMS}$) for Fp, in terms of the corresponding fluoresence intensities (IF) as a function of wavelength (WL).

As illustrated in FIG. 12, in order to elicit a flavoprotein fluorescent spectrum from a tissue element, the illuminating radiation must be within the flavoprotein excitation spectrum, typically at a wavelength of between about 400 nm and 470 nm.

Figure 13:
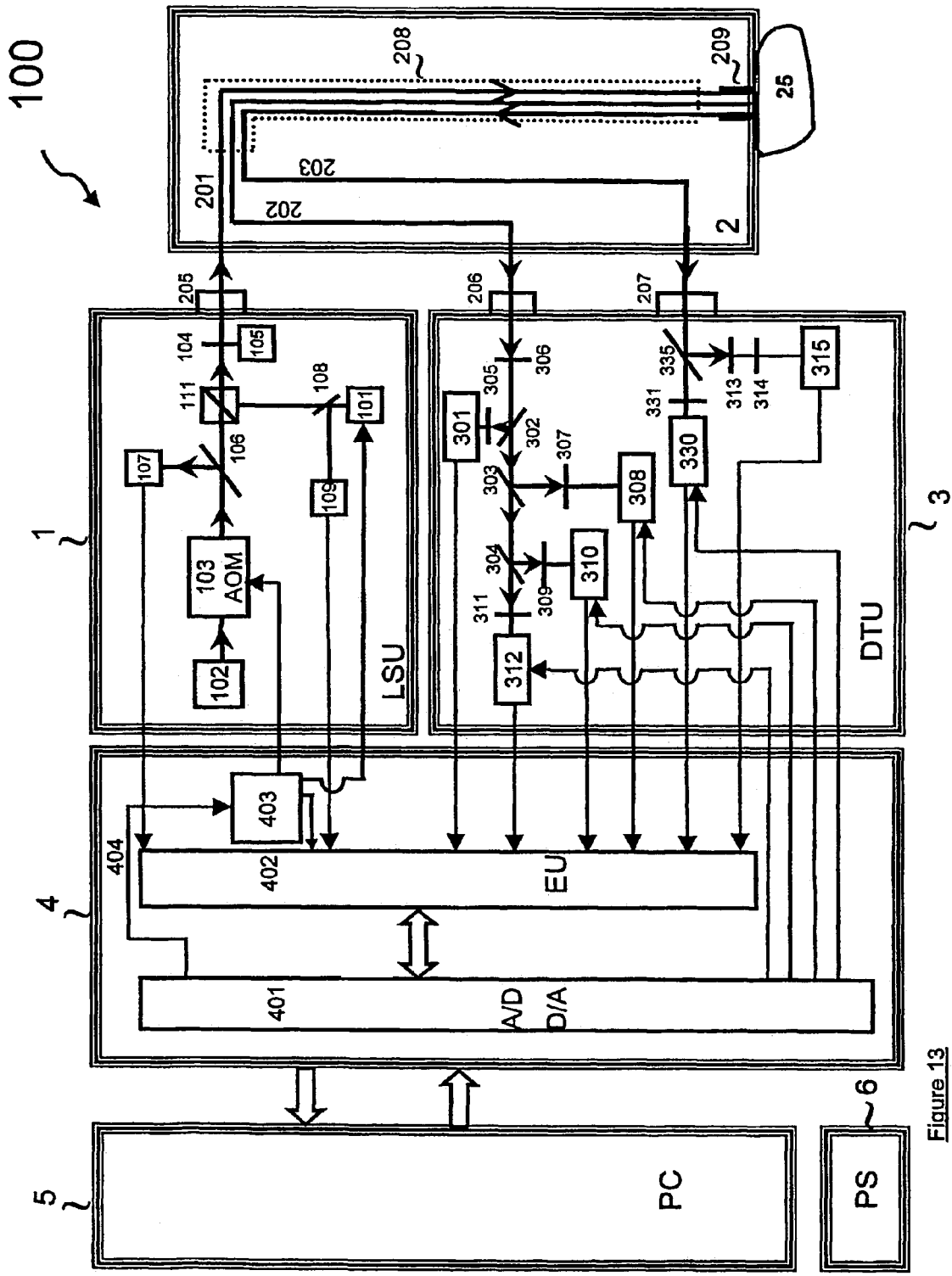
FIG. 13 illustrates schematically the main components of the third embodiment of the first aspect of the present invention.

The third embodiment of the present invention comprises similar components as previous embodiments, viz LSU (1) probes (2), DTU (3), EU (4) PC (5), PS (6) as described with respect to the first and second embodiments, in particular the first embodiment, mutatis mutandis, with the following exceptions. The DTU (3) of the fourth embodiment, as shown in FIG. 13, though substantially similar to the DTU of the first embodiment FIG. 5), further comprises the additional feature that the fluorescent radiation from the tissue is passed through beam splitter (335) filter (331) and fourth PMT detector (330). Appropriate modification to the conditioning electronics of the EU (4) and the software running on the PC (5) as described for the first embodiment is required for the third embodiment.

Thus, the third embodiment enables measurement of the flavoprotein concentration, i.e., Fp tissue viability parameter, in additional to the four above-mentioned parameters of the first embodiment. While in the first embodiment of the invention, the choice of laser light for source (102) as used for LDF monitoring is typically of a wavelength above 440 nm as described above, in order to measure the Fp fluorescence by the same light source (102) its wavelength should be limited, rather, to be within the excitation spectrum of the Fp, and not beyond the same. In the third embodiment the excitation wavelength of light source (102), which used for Doppler measurements, is chosen to lie within the excitation spectrum of Fp (i.e., in the range of about 440 nm to about 470 nm) and preferably around the Fp absorption peak, which is in the range of about 440 nm to about 455 nm. As with the first embodiment, the two sets of tissue viability measurements are made using the same excitation and two corresponding groups of collection fibers, and the same layer element of tissue is monitored for both sets of parameters—the first set including blood flow and $F_p$, and the second set including NADH, blood volume and blood oxygenation state.

In the third embodiment, a similar light sources (101) and (102) as in the first embodiment may be used. As in the first embodiment, the wavelength for light source (101) can be any wavelength that is inside the absorption spectrum of the NADH molecule, i.e. from about 315 mn to about 395 nm. To avoid the Haemodynamic artifact, and to enable measurement of oxy-deoxy haemoglobin, this wavelength is preferred to be at one of the haemoglobin oxy-deoxy isosbestic points in this bandwidth, as with the second embodiment. There is no requirement for laser Doppler measurements or for the Fp fluorescence measurements to be performed at one of these isosbestic wavelengths, since both of these measurements are normalized to the total reflection. The Doppler signal is normalized according to the Doppler algorithm, the Fp signal is normalized or corrected by the reflection measurement similarly to the NADH correction as described above. Therefore the excitation light source for (102) may be any suitable laser diode that operates within the aforesaid 400 nm to 470 nm range.

Essentially, the Fp measurement is very similar to that of NADH. The Fp excitation is by monochromatic light at a wavelength within the Fp absorption spectrum. In the present invention, this monochromatic light is provided by, and at the wavelength of, the laser light source (102). The Fp fluorescence is measured by measurement of fluorescence intensity of the fluorescence emission at single wavelength, which is within the emission fluorescence spectrum.

As with the NADH fluorescence parameter, problem of haemodynamic artifact is also relevant to Fp measurements, and compensation for this artifact is similar to that for the NADH measurements. For the Fp parameter, reflection is measured at the wavelength of the excitation of the Fp fluorescence. This wavelength, in the present invention, is also the wavelength of the Doppler LDF measurement. In the embodiments described herein, the same detector that measures Doppler LDF also measures the reflection at the same wavelength since it is the intrinsic Doppler measurement of measurement of AC signal that is superimposed on the DC reflection signal. This reflection value is subtracted from the Fp fluorescence value (in the same manner as in NADH measurements) in order to get corrected Fp fluorescence values. This typifies the compensation procedure.

As with the NADH parameter, it is preferable to measure the Fp emission (fluorescence) at oxy-deoxy isosbestic points such as 530 nm or 546 nm or 570 nm. Otherwise the fluorescence value will be influenced by the blood oxygenation.

Regarding fluorescence excitation for Fp, if only Doppler or only Fp is measured, and there is no need for the reflection measurements for evaluation of blood volume, then any excitation wavelength can be used, and does not need to be restricted to an isosbestic wavelength. Indeed as far as the Fp measurements are concerned, the reflection is measured, and used for correcting for the haemodynamic artifact, but the reflection measurements will not correctly represent blood volume changes since they will be influenced by blood oxygenation. However, it is important to provide a reflection that represents the blood volume, and for this reflectance must be measured when excitation is at an isosbestic point. Thus, either the NADH excitation is chosen to be at a corresponding isosbestic point, or the Fp excitation is chosen to be at an isosbestic point. At least one of these conditions is thus required, wherein the second parameter may be monitored by using an excitation wavelength that is not at an isosbestic wavelength. While there is generally no intrinsic advantage in either one, the availability of suitable light sources at the desired illuminating wavelengths generally decides the issue.

While it is advantageous to measure both NADH and Fp, providing either only one or only the other for a tissue element is also valuable.

Determination of the blood flow rate and of the second set of tissue viability parameters—NADH, blood volume and blood oxygenation state—in the third embodiment is as described for the first embodiment, mutatis mutandis. Further, and referring to FIG. 13, the signal from photodiode detector (301) is used for the reflection measurements for blood volume parameter. Thus, the light from the collecting fiber (202) enters the DTU (3) via optical connector (206). The collimating lens (306) collimates the light towards the beam splitter or dichroic mirror (302), which splits off the excitation light wavelength, which is then channeled towards a low-noise, fast photodiode detector (301), a condensing lens (305) being typically used in order to fill the photo-detector active area. The signal from the photodiode detector is used to perform the reflection measurements for the blood volume parameter.

As with the first embodiment, detectors (308), (310) and (312) enable monitoring of the NADH, blood oxygenation state, mutatis mutandis. In the third embodiment, a dichroic beam splitter (335) is provided to split the light provided by collection fiber (203). Part of the split light is used for the blood flow rate measurements, conducted via detector (315), as in the first embodiment, after passing through filter (313) and a condensing lens (314). The second part of the split light continues is subjected to additional filtering by a suitable filter (331), preferably a 530 nm interference filter (such as a DF20, for example), and the filtered light is incident on a fourth photo-multiplying tube (PMT) (330). The precision of all above mentioned filters are about ±5 nm.

The timing of sample and hold synchronous detection of the detectors involved in DTU (3) may be configured as follows.

When the light source (102) of WL1 for Doppler and Fp excitation is ON the detector (315) and (330) are gated. This enables measurement of Doppler and Fp fluorescence.

When the light source (101) of WL2 for NADH excitation is ON the detectors (301), (308), (310) and (312) are gated. This enables measurement of NADH fluorescence, reflection at NADH excitation wavelength and blood oxygenation.

Thus, the third embodiment may be used in a similar way to that described for the first embodiment, mutatis mutandis.

Figure 14:
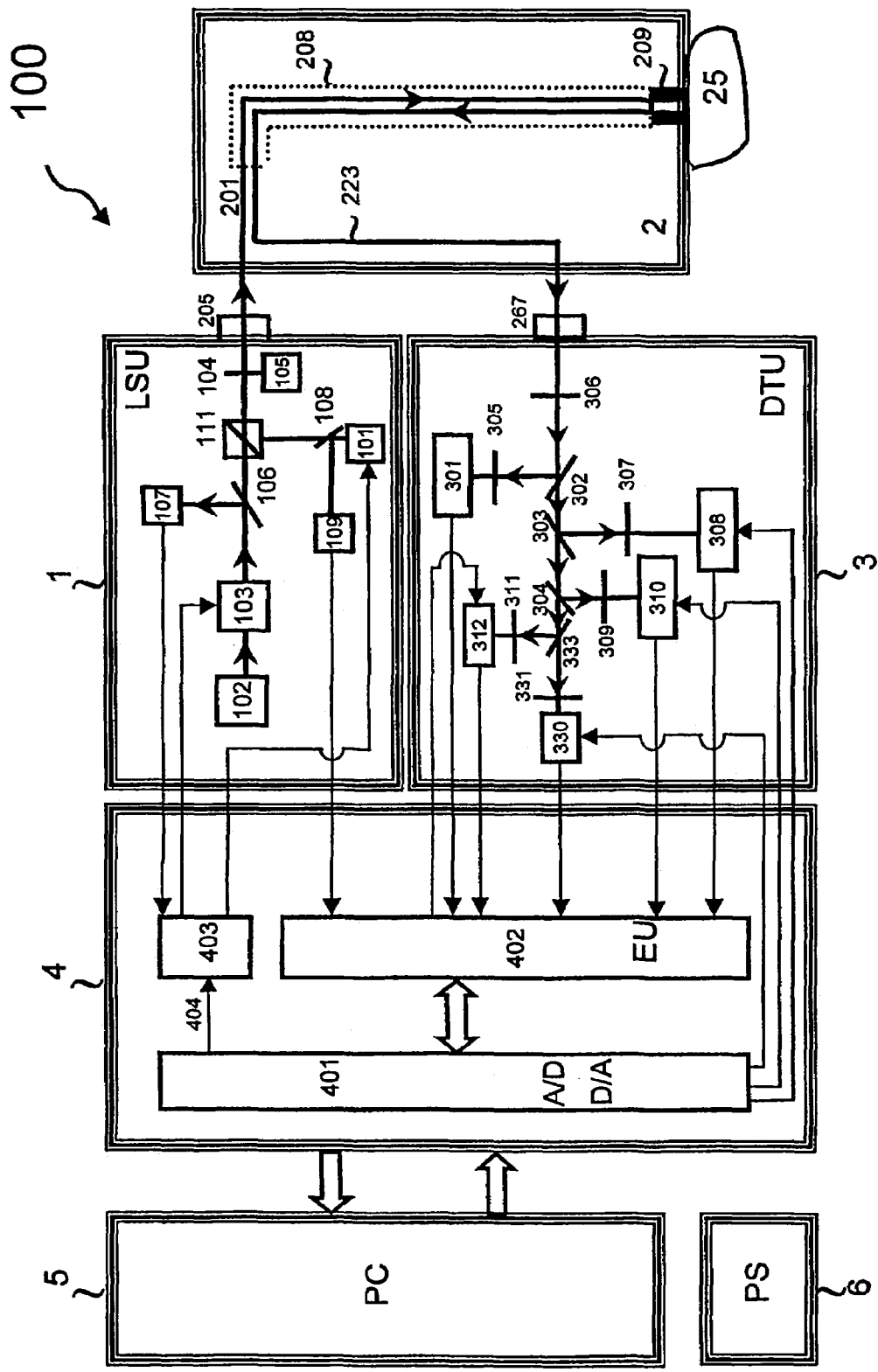
FIG. 14 illustrates schematically the main components of the fourth embodiment of the first aspect of the present invention.

The fourth embodiment of the present invention comprises similar components as previous embodiments, viz LSU (1) probes (2), DTU (3), EU (4) PC (5), PS (6) as described with respect to the first and second embodiments, in particular the second embodiment, mutatis mutandis, with the following exceptions. The DTU (3) of the fourth embodiment, as shown in FIG. 14, though substantially similar to the DTU of the second embodiment (FIG. 8), further comprises the additional feature that the fluorescent radiation from the tissue is passed through beam splitter (333) filter (331) and fourth PMT detector (330). Appropriate modification to the conditioning electronics of the EU (4)

and the software running on the PC (5) as described for the second embodiment is required for the fourth embodiment.

Thus, the fourth embodiment enables monitoring of the flavoprotein concentration, i.e., Fp tissue viability parameter, in additional to the four above-mentioned parameters of the second embodiment. While in the second embodiment of the invention, the choice of laser light for source (102) as used for LDF monitoring is limited to the 315–440 nm range as described above, in order to measure the Fp fluorescence by the same light source (102) its wavelength should be limited, rather, to be within the excitation spectrum of the Fp and not within the excitation spectrum of NADH. In the fourth embodiment the excitation wavelength of light source (102), which is used for Doppler measurements, is chosen to lie within the excitation spectrum of Fp (i.e., in the range of about 400 nm to about 470 nm therefore the excitation wavelengths for light source (102) are limited to the range of about 400 nm to 440 nm. As with the second embodiment, all tissue viability measurements are made using the same excitation and using the corresponding collection fibers, and virtually the same volume element of tissue is monitored for both sets of parameters—the first set including blood flow and $F_p$, and the second set including NADH, blood volume and blood oxygenation state.

In the fourth embodiment, as in the second embodiment, a light source (101) such as, for example, filtered spectral lamp, light emitting diode LED, laser diode or pulsed laser, may be used for excitation of NADH fluorescence. The light source wavelength can be any wavelength that is inside the absorption spectrum of the NADH molecule, in the range of from about 315 nm to about 395 nm. To avoid the Haemodynamic artifact, and to enable measurement of oxy-deoxy haemoglobin, this wavelength is preferred to be at one of the haemoglobin oxy-deoxy isosbestic points in this bandwidth, as with the second embodiment. There is no requirement for laser Doppler measurements or for the Fp fluorescence measurements to be performed at one of these isosbestic wavelengths, since both of these measurements are normalized to the total reflection. The Doppler signal is normalized according to the Doppler algorithm, the Fp signal is normalized or corrected by the reflection measurement similarly to the NADH correction as described above. Therefore the excitation light source for (102) may be any low noise CW laser such as Nichia blue laser diode, for example.

Determination of the blood flow rate and of the second set of tissue viability parameters—NADH, blood volume and blood oxygenation state—in the fourth embodiment is as described for the second embodiment, mutatis mutandis. Further, and referring to FIG. 14, the signal from photodiode detector (301) is used for LDF blood flow rate monitoring as well as the reflection measurements for blood volume parameter for Fp and NADH correction. Thus, the light from the collecting fiber (223) enters the DTU (3) via optical connector (267). The collimating lens (306) collimates the light towards the beam splitter or dichroic mirror (302), which splits off the excitation light wavelength, which is then channeled towards a low-noise, fast photodiode detector (301), a condensing lens (305) being typically used in order to fill the photo-detector active area. The signal from the photodiode detector is used to perform both Doppler and Reflection measurements.

Thus the reflection at both detection wavelengths (WL1) and (WL2) will, in this embodiment, pass through the same collecting fiber (223). The separation of these different signals is typically achieved by time-sharing. The light sources (102) and (101) are typically working in "chopping mode", and therefore each source is ON only for a short time period as is described hereinafter. Each light source has a low duty cycle, therefore there is plenty of time to turn ON one light source while the other one in still in the OFF period. Each one of the corresponding detectors (107) and (109) is synchronously sampled at the correct timing in order to get intensity information regarding the corresponding excitation source. The detector (301) is sampled twice, once for the measurement of reflection at WL1 and corresponding laser Doppler measurements and a second time, for reflection measurement at WL2.

In case that the Doppler excitation wavelength WL1 will be lower then 420 nm, both reflections at WL1 and WL2 have substantially lower wavelengths than the NADH fluorescence and therefore the same dichroic beam splitter (302) can be used for separating these two relatively strong reflections from the weaker fluorescence signal. On the other hand, if the Doppler excitation wavelength WL1 will have a wavelength that higher then about 420 nm, the dichroic beam splitter (302) cannot be used since the NADH fluorescence light will not pass through it. Therefore in such a case the dichroic beam splitter (302) should be replaced by simple beam splitter of for example 1:10 ratio in order to split to the detector (301) a small part of the desired reflection intensity at the excitation wavelengths. This also enables transmission of the similar wavelengths of the NADH and Fp fluorescence to all another detectors namely (308), (310), (312) and (330). It should be emphasized that the strong intensity of the reflection at WL1 will not interfere the NADH fluorescence measurements since these signals are uncorrelated in the time domain. Similarly, there is no interference with the Fp fluorescence measurements since an interference filter (314) is used, as described below.

Light of wavelengths higher than the excitation wavelength WL1 or WL2 passes through the dichroic mirror or beam splitter (302) and is incident on a second dichroic beam-splitter (303), which is selected to reflect wavelengths lower then about 440 nm and to transmit all higher wavelengths. The reflected light beam is passed through a suitable filter (307), preferably a 435 nm (10DF) filter, and is then fed into a first photo-multiplying tube (PMT) (308). The light transmitted through the second dichroic beam-splitter (303) is subjected to additional splitting by a third dichroic beam-splitter (304) that reflects wavelengths lower then 460 nm, but is transparent to higher wavelengths. The reflected light from the third dichroic beam splitter (304) is filtered by a suitable filter (309), preferably a 455 nm (10DF) filter, and is then incident on a second photo-multiplying tube (PMT) (310). This wavelength is close to an oxy-deoxy isosbestic point, so the fluorescence intensity as measured by this PMT (310) correlates directly with the NADH fluorescence. The light that passes through the third dichroic beam-splitter (304) is subjected to additional splitting by a fourth dichroic beam-splitter (333) that reflects wavelengths lower then 485 nm, but is transparent to higher wavelengths. The reflected light pass additional filtering by a suitable filter (311), preferably a 475 nm interference filter (DF10), and the filtered light is incident on a third photo-multiplying tube (PMT) (312). The light that pass the dichroic beam-splitter (333) comprises wavelengths higher then 485 nm and comprises the Fp fluorescence emission. This light is subjected to additional filtering by a suitable filter (331), preferably a 530 nm interference filter (such as a DF20, for example), and the filtered light is incident on a fourth photo-multiplying tube (PMT) (330). The precision of all above mentioned filters are about ±5 nm.

The timing of sample and hold, synchronous detection of the detectors involved in DTU (3) may be configured as follows.

When the light source (102) of WL1 for Doppler and Fp excitation is ON the detector (301) and (330) are gated. This enables measurement of Doppler, Reflection at Fp excitation wavelength and Fp fluorescence.

When the light source (101) of WL2 for NADH excitation is ON the detectors (301), (308); (310) and (312) are gated. This enables measurement of NADH fluorescence, Reflection at NADH excitation wavelength and blood oxygenation.

Thus, the fourth embodiment may be used in a similar way to that described for the second embodiment, mutatis mutandis.

Figure 11:
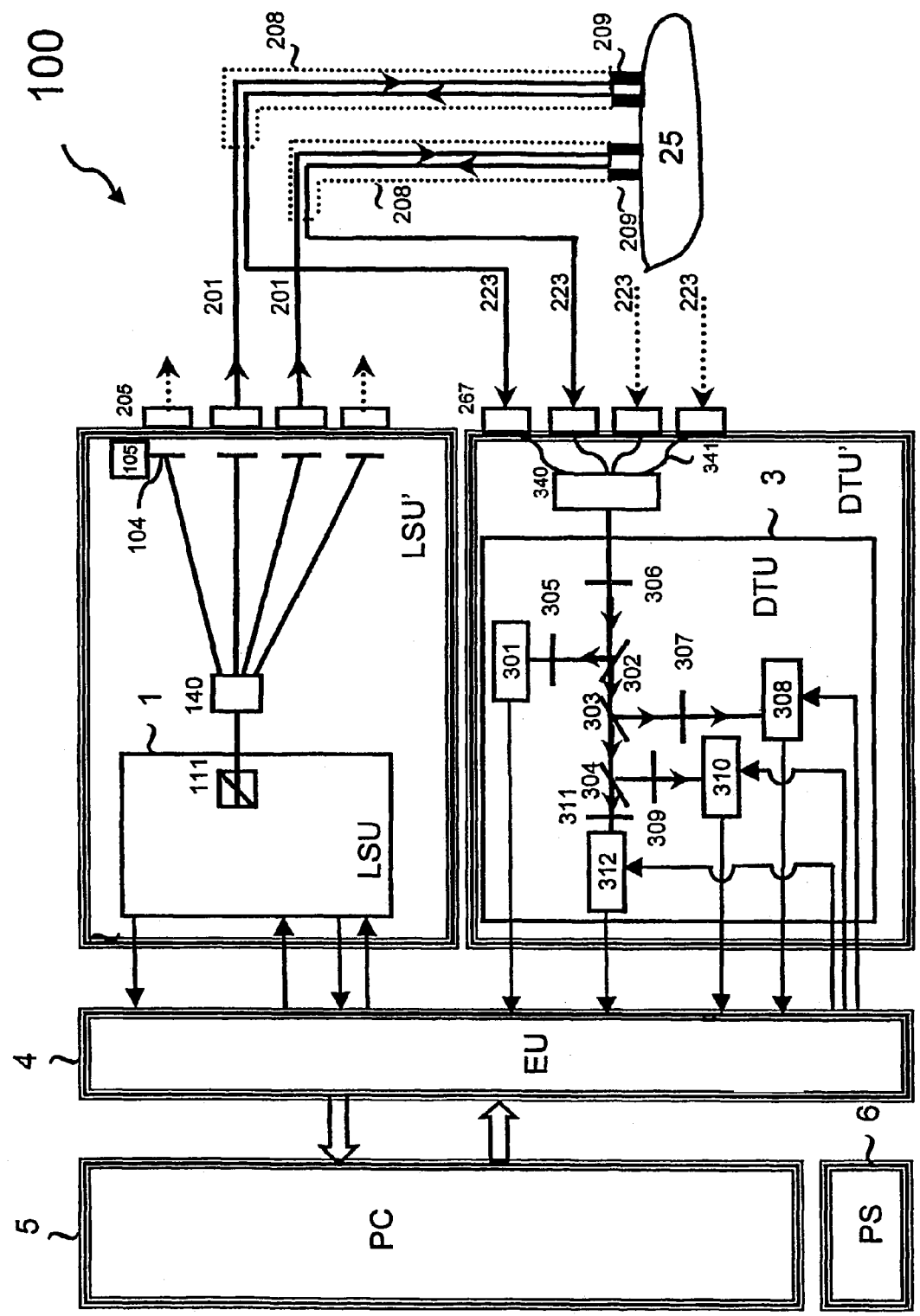
FIG. 11 illustrates a fifth embodiment of the present invention comprising a plurality of probes.

In some clinical procedures it is desirable to monitor the blood parameters for the assessment of organ tissue vitality in different regions of the body. In these situations, a multiple probe system is desirable. By way of example, a fifth embodiment of the present invention, consisting of a multi-probe system is shown in FIG. 11. This embodiment as illustrated, uses a plurality of probes, each probe being substantially the same as those described in the second embodiment. It will be appreciated however, that a plurality of the probe according to the first embodiment could be used, or, alternatively one or more probes according to each one of the first and second embodiments, mutatis mutandis. Clearly, any given probe comprised in the system may be adapted to monitor the same or different parameter to any one of the other probes therein.

The chopping feature, which provide advantages in minimising exposure of the probed tissue to dangerous illumination levels, also facilitates a diversion of the irradiation light to any one of a plurality of probes, and subsequent detection of the return signals therefrom, by effectively time-sharing the detection unit (DTU) between the probes. In other words, the multiprobe detection system essentially multiplexes the signals obtained from each of the plurality of probes, situated in different parts of the tissue or organs.

The fifth embodiment of the present invention comprises similar components as previous embodiments, viz LSU (1) probes (2), DTU (3), EU (4) PC (5), PS (6) as described with respect to the first and second embodiments, mutatis mutandis, with the following exceptions. The LSU (1) of the fifth embodiment, as shown in FIG. 11, though substantially similar to the LSU of the second embodiment (FIG. 8), further comprises the additional feature that the excitation light is passed through an acousto-optic deflector (AOD) (140) before being coupled and deflected to a plurality of excitation fibers by a corresponding plurality of lenses (104), each one being mounted on one of a plurality of adapters (105). The LSU of the fifth embodiment is thus connected by said plurality of excitation fibers to a corresponding plurality of fiber optic probes, each probe being coupled via an optical connector (205). In the third embodiment, the collecting fiber (223) from each probe is thus connected to the DTU (3) by an optical connector (267) that is essentially similar to that used in the second embodiment. The radiation received via the optical connectors (267) is coupled to a common optical coupler (340) via corresponding optical fibers (341). The optical coupler (340) and plurality of optical connectors (267) of this fifth embodiment replaces the single optical connector (267) described in the second embodiment. From the optical coupler (340) the light passes through a collimating lens (306) and on to the detection equipment of the DTU (3) as described for the second embodiment mutatis mutandis. Appropriate modification to the conditioning electronics of the EU (4) and the software running on the PC (5) as described for the second embodiment is required for the fifth embodiment.

For embodiments of the multi-probe system comprising a plurality of probes according to the first embodiment, a corresponding plurality of connectors (206) and of connectors (207) (which are in turn appropriately connected to corresponding ones of a plurality of fibers (202) and (203)) are connected to one of two optical couplers. The optical coupler that couples the (206) connectors may then be connected by the, existing arrangement of filters and beamsplitters to the PMTs (301), (308), (310) and (312) as shown in FIG. 5, and the optical coupler that couples the (207) connectors may then be connected by the existing arrangement of optical components to the PMT (315).

It should also be noted that multi-tissue element monitoring could also be accomplished by a plurality of probes, each one having a dedicated light source and associated optical components (LSU) and detection system (DTU), with each probe unit being controlled by the same PC and EU units, and being powered using the same PS.

The fifth embodiment may be operated in a variety of modes as required by the clinical situation and diagnostic needs to which it is applied. Two particular modes of monitoring for which such multiple probe systems can be usefully applied, are described:

In the first mode, the mean signal intensities from the multiplicity of probes is calculated and displayed. This results in the parameters detected representing an average response of the multiplicity of tissue volumes probed, and will generally, better reflect the state of the organ layer as a whole. This mode of monitoring could be useful in transplantation surgery when better monitoring of the viability of donated organs are needed.

In the second mode, by applying one or several of the plurality of probes to each of several locations on the same organ or several different locations of different organs, the quasi-continuous monitoring of these organs over the same time period can be achieved by multiplexing the signals from the individual probes, with the parametric response of each organ being separately monitored and displayed.

The electronics and the software for the first mode will be substantially similar to that described with respect to the second embodiment. The main difference being that the chopping sequences used, and the sampling rate per probe, are engineered and optimized depending on number of probes, patient condition, and tissue type under observation.

The $t_{on}$ period per probe remains the same as for the single probe embodiment, but in the OFF time for aforementioned probe, additional probes are excited and measured. Accordingly, the timing of the AOD (140) is correlated with the sequence shown in FIG. 7(*a*) so that each subsequent pulse is delivered to the subsequent probe. After appropriate smoothing, the output signals from each detector are used to generate a value for the desired blood viability parameter, corresponding of the mean value for the plurality of monitored tissue volumes, and thus more representative of the viability of the organ as a whole.

The second measurement mode of the fifth embodiment requires the same chopping sequence as that required by the first mode. The (S/H) circuits and the accompanying data acquisition system in the EU (4) are somewhat different however. For tracking the various monitored parameters for each probe separately, using the same system, the (S/H) circuits shown in FIGS. 9(*a*) and 9(*b*) may be advantageously performed by fast multi input analog to digital (A/D) converters. This requires that the fast A/D system (410) receives the detector signals directly without the signal conditioning electronics (402) that were used in the second embodiment. The fast A/D converter (401) will digitize the detector signal for at each time period and the sampled values for each probe and each measured parameter will be stored in the temporary memory of the PC (5). Since the whole information, that is all signals for each probe is available in the computer, the signal from each probes can be processed separately, allowing the vitality parameters of each monitored tissue volume, corresponding to different organs to be monitored and displayed on the screen.

A sixth embodiment of the present invention (not illustrated) comprises all the elements of the fifth embodiment as described herein, mutatis mutandis, wherein the DTU is modified in a similar manner to that described for the third embodiment, mutatis mutandis, enabling the multi-probe system to monitor Fp fluorescence as well as the blood flow rate and the three parameters of the second set of parameters, at a plurality of locations.

In each one of the first through sixth embodiments, the signals provided by the various detectors are fed to the PC (5) and converted to suitable corresponding values of blood flow rate, NADH fluorescence, blood oxygenation state, blood volume and Fp fluorescence, via suitable algorithms, correlations, tables and so on, in a manner known in the art.

While specific embodiments of the invention have been described for the purpose of illustration, it will be understood that the invention may be carried out in practice by skilled persons with many modifications, variations and adaptations, without departing from its spirit or exceeding the scope of the claims.

The invention claimed is:

1. Apparatus for monitoring viability of a tissue element comprising:
   a) at least one light source that illuminates the tissue element from at least one illumination location with at least first illuminating radiation at a first wavelength and second illuminating radiation at a second wavelength;
   b) first and second radiation receivers located at first and second distances from the at least one illumination location respectively and at least one radiation detector operatively coupled with said first and second radiation receivers which generates first and second signals respectively responsive to illuminating the tissue element with the first and second illuminating radiations; and
   C) a processor that processes the signals to determine first and second tissue viability parameters for the tissue element;
wherein the first and second distances are determined responsive substantially only to the first and second wavelengths and tissue characteristics so that sample depths for the first and second illuminating radiations are substantially equal; and further
wherein the first tissue viability parameter is different than the second tissue viability parameter.

2. Apparatus as claimed in claim 1, wherein a ratio of said first distance to said second distance is substantially correlated to a ratio of said second wavelength to said first wavelength.

3. Apparatus as claimed in claim 1, wherein said first wavelength is substantially different from said second wavelength.

4. Apparatus according to claim 3, wherein the scattering coefficient in the tissue element differs substantially for light of the first and second wavelengths.

5. Apparatus according to claim 3, wherein the absorption coefficient in the tissue element differs substantially for light of the first and second wavelengths.

6. Apparatus as claimed in claim 1, wherein said first wavelength and said second wavelength have substantially similar penetration depth with respect to said tissue element.

7. Apparatus as claimed in claim 6, wherein a ratio of said first distance to said second distance is substantially unity.

8. Apparatus as claimed in claim 6, wherein said first wavelength is substantially the same as said second wavelength.

9. Apparatus as claimed in claim 8, wherein said first radiation receiver and said second radiation receiver are comprised of at least one common third optical fiber capable of being brought into registry with said tissue element.

10. Apparatus as claimed in claim 9, wherein the at least one illumination location comprises a common illumination location for the first and second illumination radiation, provided by at least one excitation optical fiber capable of being brought into registry with said tissue element.

11. Apparatus as claimed in claim 10, wherein said at least one excitation optical fiber and said at least one common third optical fiber are housed in a suitable probe head.

12. Apparatus as claimed in claim 1, wherein said light source of the second illuminating radiation comprises a suitable monochromatic light source.

13. Apparatus as claimed in claim 12, wherein second wavelength is chosen to lie at a suitable isosbestic point.

14. Apparatus as claimed in claim 13, wherein said isosbestic point is within a substantially isosbestic range of the oxyhaemoglobin-deoxyhaemoglobin absorption vs. wavelength curves.

15. Apparatus as claimed in claim 12, wherein said second wavelength is within the range of wavelengths corresponding to a NADH excitation spectrum.

16. Apparatus as claimed in claim 12, wherein said second wavelength is between about 300 nm and about 395 nm.

17. Apparatus as claimed in claim 12, wherein said second wavelength is within about ±5 nm of any of the following wavelengths: 325 nm, 337 nm, 349 nm, 355 nm, 366 nm, 370 nm, 384 nm or 390 nm.

18. Apparatus as claimed in claim 12, wherein said second illuminating radiation is provided by any suitable UV light source.

19. Apparatus as claimed in claim 1, wherein said second tissue viability parameter is NADH concentration, and said second radiation received by said second radiation receiver is an NADH fluorescence emitted by the tissue element in response to illumination thereof by said second illuminating radiation, said second tissue viability parameter being provided by the intensity of said NADH fluorescence.

20. Apparatus as claimed in claim 19, wherein said at least one detector comprises a second detector for detecting said second radiation received by said second radiation receiver.

21. Apparatus as claimed in claim 1, wherein said second tissue viability parameter is blood volume within said tissue element, and said second radiation received by said second radiation receiver is a reflection from the tissue element in response to illumination thereof by said second illuminating radiation; the said second tissue viability parameter being provided by the intensity of said reflection.

22. Apparatus as claimed in claim 21, wherein said at least one detector comprises a third detector for detecting said second radiation received by said second radiation receiver.

23. Apparatus as claimed in claim 1, wherein said second tissue viability parameter is blood oxygenation ratio within said tissue element, and said second radiation received by said second radiation receiver is a fluorescence emitted by the tissue element in response to illumination thereof by said second illuminating radiation, said second tissue viability parameter being provided by the intensity of said fluorescence at least at two fluorescent wavelengths.

24. Apparatus as claimed in claim 23, wherein one of said at least two fluorescent wavelength is chosen to lie at an oxy-deoxy fluorescence emission isosbestic point.

25. Apparatus as claimed in claim 23, wherein one of said at least two fluorescent wavelengths is higher and another one of said at least two fluorescent wavelengths is smaller than a wavelength corresponding to an oxy-deoxy fluorescence emission isosbestic point.

26. Apparatus as claimed in claim 23, wherein said at least one detector comprises a fourth detector for detecting said second radiation received by said second radiation receiver.

27. Apparatus according to claim 1, wherein the first tissue viability parameter is a blood flow rate tissue viability parameter.

28. Apparatus as claimed in claim 27, wherein said light source of the first illuminating radiation comprises a coherent light source.

29. Apparatus as claimed in claim 28 wherein said blood flow rate tissue viability parameter is provided by the Doppler shift of said first radiation received by said first radiation receiver with respect to the said first illuminating radiation.

30. Apparatus as claimed in claim 29, wherein said at least one detector comprises a first detector for detecting said first radiation received by said first radiation receiver.

31. Apparatus as claimed in claim 28, wherein said coherent light source is a laser light source.

32. Apparatus as claimed in claim 31, wherein said laser light source is adapted to provide said first illuminating radiation of said first wavelength in pulses of predetermined duration and intensity.

33. Apparatus as claimed in claim 32, further comprising a suitable controller for controlling the frequency of pulsing of said pulses.

34. Apparatus as claimed in claim 33, wherein said controller is further adapted to provide said pulses in packages of pulses, each package comprising at least one pulse and separated from a preceding or following package by a predetermined time period.

35. Apparatus as claimed in claim 34, wherein said predetermined time period is greater than the time interval between consecutive pulses within a package.

36. Apparatus as claimed in claim 35, wherein said time period is controllably variable.

37. Apparatus as claimed in claim 34, wherein the number of pulses within each package is controllably variable.

38. Apparatus as claimed in claim 34, wherein said controller is operatively connected to said at least one detector.

39. Apparatus as claimed in claim 33, wherein said controller is selectively responsive to previously detected signals corresponding to the detection of said second radiation detected by means of said at least one detector.

40. Apparatus as claimed in claim 27, wherein said first wavelength is between about 300 nm and about 440 nm.

41. Apparatus as claimed in claim 27, wherein said first wavelength is greater than about 440 nm and is within the visible or near infrared wavelength range.

42. Apparatus as claimed in claim 27, wherein said first wavelength is either in the range 410±30 nm or within about ±5 nm of any one of the following wavelengths: 355 nm, 430 nm, 440 nm, 455 nm, 460 nm, 490 nm, 532 nm or 805 nm.

43. Apparatus as claimed in claim 27, for further monitoring a flavoprotein concentration tissue vitality parameter, wherein said at least one detector comprises a fifth detector for detecting a portion of said first radiation received by said first radiation receiver, said portion of said received first radiation being a flavoprotein fluorescence emitted by said tissue element in response to illumination thereof by said first illuminating radiation, said flavoprotein tissue viability parameter being provided by the intensity of said flavoprotein fluorescence.

44. Apparatus as claimed in claim 43, wherein said first wavelength is within the range of wavelengths corresponding to a flavoprotein excitation spectrum.

45. Apparatus as claimed in claim 43, wherein said first wavelength is between about 440 nm and 470 nm.

46. Apparatus according to claim 1, wherein the at least one illumination location comprises a common illumination location for the first and second illuminating radiation.

47. Apparatus as claimed in claim 46, wherein said common illumination location is provided by at least one excitation optical fiber capable of being brought into registry with said tissue element.

48. Apparatus as claimed in claim 47, wherein said first radiation receiver comprises at least one suitable first receiving optical fiber capable of being brought into registry with said tissue element.

49. Apparatus as claimed in claim 48, wherein said second radiation receiver comprises at least one suitable second receiving optical fiber capable of being brought into registry with said tissue element.

50. Apparatus as claimed in claim 49, wherein said at least one excitation optical fiber, said at least one first receiving optical fiber and said at least one second receiving optical fiber are housed in a suitable probe head.

51. Apparatus according to claim 1, wherein the first and second radiation receivers comprise a probe, and the at least one light source illuminates the tissue element through the probe.

52. A method for monitoring first and second tissue viability parameters of a tissue element, the method comprising:

a) illuminating the tissue element from at least one illumination location with first and second illuminating radiations at respectively first and second wavelengths;

b) determining first and second distances from the at least one illumination location responsive substantially only to the first and second wavelengths and tissue characteristics so that sample depths for the first and second illuminating radiations for the first and second distances are substantially equal;

c) receiving radiations at the first and second distances responsive respectively to illuminating the tissue element with the first and second illuminating radiation, and generating first and second signals responsive thereto;

d) determining first and second tissue viability parameters responsive to the first and second signals; and e) outputting an indication of tissue viability based on said determined tissue viability parameters.

* * * * *